United States Patent
Levine et al.

(10) Patent No.: US 12,172,017 B2
(45) Date of Patent: Dec. 24, 2024

(54) VAGUS NERVE STIMULATION TO TREAT NEURODEGENERATIVE DISORDERS

(71) Applicant: SetPoint Medical Corporation, Valencia, CA (US)

(72) Inventors: Jacob A. Levine, West Hempstead, NY (US); Nicole Hamlin, Centereach, NY (US); David Chernoff, Valencia, CA (US)

(73) Assignee: SetPoint Medical Corporation, Valencia, CA (US)

( * ) Notice: Subject to any disclaimer, the term of this patent is extended or adjusted under 35 U.S.C. 154(b) by 0 days.

(21) Appl. No.: 16/158,222

(22) Filed: Oct. 11, 2018

(65) Prior Publication Data

US 2019/0111263 A1  Apr. 18, 2019
US 2022/0072309 A9  Mar. 10, 2022

Related U.S. Application Data

(63) Continuation-in-part of application No. 15/853,350, filed on Dec. 22, 2017, which is a continuation of
(Continued)

(51) Int. Cl.
*A61N 1/36* (2006.01)
*A61B 5/388* (2021.01)
(Continued)

(52) U.S. Cl.
CPC .......... *A61N 1/36053* (2013.01); *A61B 5/388* (2021.01); *A61N 1/36175* (2013.01);
(Continued)

(58) Field of Classification Search
CPC ............ A61N 1/36053; A61N 1/36175; A61N 1/36103; A61N 1/36082; A61N 1/36067;
(Continued)

(56) References Cited

U.S. PATENT DOCUMENTS 2,164,121 A    6/1939  Pescador
3,363,623 A    1/1968  Atwell
(Continued)

FOREIGN PATENT DOCUMENTS

CN    201230913 A    5/2009
CN    101528303 A    9/2009
(Continued)

OTHER PUBLICATIONS

US 6,184,239 B1, 02/2001, Puskas (withdrawn)
(Continued)

*Primary Examiner* — Shirley X Jian
(74) *Attorney, Agent, or Firm* — Shay Glenn LLP

(57) ABSTRACT

Systems, devices, and methods for using vagus nerve stimulation to treat demyelination disorders and/or disorder of the blood brain barrier are described. The vagus nerve stimulation therapy described herein is configured to reduce or prevent demyelination and/or promote remyelination to treat various disorders related to demyelination, such as multiple sclerosis. A low duty cycle stimulation protocol with a relatively short on-time and a relatively long off-time can be used.

22 Claims, 10 Drawing Sheets

Related U.S. Application Data application No. 14/968,702, filed on Dec. 14, 2015, now Pat. No. 9,849,286, which is a continuation of application No. 14/336,942, filed on Jul. 21, 2014, now Pat. No. 9,211,410, which is a continuation-in-part of application No. 13/467,928, filed on May 9, 2012, now Pat. No. 8,788,034.

(60) Provisional application No. 62/576,547, filed on Oct. 24, 2017, provisional application No. 62/572,374, filed on Oct. 13, 2017, provisional application No. 61/484,112, filed on May 9, 2011.

(51) Int. Cl.

| | |
|---|---|
| A61B 5/00 | (2006.01) |
| A61B 5/01 | (2006.01) |
| A61B 5/145 | (2006.01) |
| A61N 1/04 | (2006.01) |
| A61N 1/05 | (2006.01) |
| A61N 1/08 | (2006.01) |
| G01N 33/68 | (2006.01) |

(52) U.S. Cl.
CPC .............. *A61B 5/01* (2013.01); *A61B 5/145* (2013.01); *A61B 5/4029* (2013.01); *A61B 5/4041* (2013.01); *A61B 5/4076* (2013.01); *A61B 5/4842* (2013.01); *A61B 5/6877* (2013.01); *A61N 1/0456* (2013.01); *A61N 1/0556* (2013.01); *A61N 1/08* (2013.01); *A61N 1/36064* (2013.01); *A61N 1/36067* (2013.01); *A61N 1/36082* (2013.01); *A61N 1/36103* (2013.01); *C12Q 2600/158* (2013.01); *G01N 33/6896* (2013.01); *G01N 2333/78* (2013.01); *G01N 2800/2835* (2013.01); *G01N 2800/285* (2013.01); *G01N 2800/52* (2013.01); *G01N 2800/7095* (2013.01)

(58) Field of Classification Search
CPC .... A61N 1/36064; A61N 1/08; A61N 1/0556; A61N 1/0456; A61B 5/04001; A61B 5/4076; A61B 5/4029; A61B 5/01; A61B 5/145; A61B 5/4842; A61B 5/6877; A61B 5/4041; A61B 5/388; G01N 2800/7095; G01N 2800/52; G01N 2800/285; G01N 2800/2835; G01N 2333/78; G01N 33/6896; C12Q 2600/158
USPC .......................................................... 607/2
See application file for complete search history.

(56) References Cited

U.S. PATENT DOCUMENTS

| | | | |
|---|---|---|---|
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Iino et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,824,027 A | 10/1998 | Hoffer et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |

(56) References Cited

U.S. PATENT DOCUMENTS

| | | | |
|---|---|---|---|
| 6,002,964 | A | 12/1999 | Feler et al. |
| 6,006,134 | A | 12/1999 | Hill et al. |
| 6,017,891 | A | 1/2000 | Eibl et al. |
| 6,028,186 | A | 2/2000 | Tasset et al. |
| 6,051,017 | A | 4/2000 | Loeb et al. |
| 6,083,696 | A | 7/2000 | Biesecker et al. |
| 6,083,905 | A | 7/2000 | Voorberg et al. |
| 6,096,728 | A | 8/2000 | Collins et al. |
| 6,104,956 | A | 8/2000 | Naritoku et al. |
| 6,110,900 | A | 8/2000 | Gold et al. |
| 6,110,914 | A | 8/2000 | Phillips et al. |
| 6,117,837 | A | 9/2000 | Tracey et al. |
| 6,124,449 | A | 9/2000 | Gold et al. |
| 6,127,119 | A | 10/2000 | Stephens et al. |
| 6,140,490 | A | 10/2000 | Biesecker et al. |
| 6,141,590 | A | 10/2000 | Renirie et al. |
| 6,147,204 | A | 11/2000 | Gold et al. |
| 6,159,145 | A | 12/2000 | Satoh |
| 6,164,284 | A | 12/2000 | Schulman et al. |
| 6,166,048 | A | 12/2000 | Bencherif |
| 6,168,778 | B1 | 1/2001 | Janjic et al. |
| 6,171,795 | B1 | 1/2001 | Korman et al. |
| 6,205,359 | B1 | 3/2001 | Boveja |
| 6,208,894 | B1 | 3/2001 | Schulman et al. |
| 6,208,902 | B1 | 3/2001 | Boveja |
| 6,210,321 | B1 | 4/2001 | Di Mino et al. |
| 6,224,862 | B1 | 5/2001 | Turecek et al. |
| 6,233,488 | B1 | 5/2001 | Hess |
| 6,266,564 | B1 | 7/2001 | Hill et al. |
| 6,269,270 | B1 | 7/2001 | Boveja |
| 6,304,775 | B1 | 10/2001 | Iasemidis et al. |
| 6,308,104 | B1 | 10/2001 | Taylor et al. |
| 6,337,997 | B1 | 1/2002 | Rise |
| 6,339,725 | B1 | 1/2002 | Naritoku et al. |
| 6,341,236 | B1 | 1/2002 | Osorio et al. |
| 6,356,787 | B1 | 3/2002 | Rezai et al. |
| 6,356,788 | B2 | 3/2002 | Boveja |
| 6,381,499 | B1 | 4/2002 | Taylor et al. |
| 6,405,732 | B1 | 6/2002 | Edwards et al. |
| 6,407,095 | B1 | 6/2002 | Lochead et al. |
| 6,428,484 | B1 | 8/2002 | Battmer et al. |
| 6,429,217 | B1 | 8/2002 | Puskas |
| 6,447,443 | B1 | 9/2002 | Keogh et al. |
| 6,449,507 | B1 | 9/2002 | Hill et al. |
| 6,473,644 | B1 | 10/2002 | Terry, Jr. et al. |
| 6,479,523 | B1 | 11/2002 | Puskas |
| 6,487,446 | B1 | 11/2002 | Hill et al. |
| 6,511,500 | B1 | 1/2003 | Rahme |
| 6,528,529 | B1 | 3/2003 | Brann et al. |
| 6,532,388 | B1 | 3/2003 | Hill et al. |
| 6,542,774 | B2 | 4/2003 | Hill et al. |
| 6,556,868 | B2 | 4/2003 | Naritoku et al. |
| 6,564,102 | B1 | 5/2003 | Boveja |
| 6,587,719 | B1 | 7/2003 | Barrett et al. |
| 6,587,727 | B2 | 7/2003 | Osorio et al. |
| 6,600,956 | B2 | 7/2003 | Maschino et al. |
| 6,602,891 | B2 | 8/2003 | Messer et al. |
| 6,609,025 | B2 | 8/2003 | Barrett et al. |
| 6,610,713 | B2 | 8/2003 | Tracey |
| 6,611,715 | B1 | 8/2003 | Boveja |
| 6,615,081 | B1 | 9/2003 | Boveja |
| 6,615,085 | B1 | 9/2003 | Boveja |
| 6,622,038 | B2 | 9/2003 | Barrett et al. |
| 6,622,041 | B2 | 9/2003 | Terry, Jr. et al. |
| 6,622,047 | B2 | 9/2003 | Barrett et al. |
| 6,628,987 | B1 | 9/2003 | Hill et al. |
| 6,633,779 | B1 | 10/2003 | Schuler et al. |
| 6,656,960 | B2 | 12/2003 | Puskas |
| 6,668,191 | B1 | 12/2003 | Boveja |
| 6,671,556 | B2 | 12/2003 | Osorio et al. |
| 6,684,105 | B2 | 1/2004 | Cohen et al. |
| 6,690,973 | B2 | 2/2004 | Hill et al. |
| 6,718,208 | B2 | 4/2004 | Hill et al. |
| 6,721,603 | B2 | 4/2004 | Zabara et al. |
| 6,735,471 | B2 | 5/2004 | Hill et al. |
| 6,735,474 | B1 | 5/2004 | Loeb et al. |
| 6,735,475 | B1 | 5/2004 | Whitehurst et al. |
| 6,760,626 | B1 | 7/2004 | Boveja |
| 6,762,032 | B1* | 7/2004 | Nelson ............. A61K 39/39541 435/7.8 |
| 6,778,854 | B2 | 8/2004 | Puskas |
| 6,804,558 | B2 | 10/2004 | Haller et al. |
| RE38,654 | E | 11/2004 | Hill et al. |
| 6,826,428 | B1 | 11/2004 | Chen et al. |
| 6,832,114 | B1 | 12/2004 | Whitehurst et al. |
| 6,838,471 | B2 | 1/2005 | Tracey |
| RE38,705 | E | 2/2005 | Hill et al. |
| 6,879,859 | B1 | 4/2005 | Boveja |
| 6,885,888 | B2 | 4/2005 | Rezai |
| 6,901,294 | B1 | 5/2005 | Whitehurst et al. |
| 6,904,318 | B2 | 6/2005 | Hill et al. |
| 6,920,357 | B2 | 7/2005 | Osorio et al. |
| 6,928,320 | B2 | 8/2005 | King |
| 6,934,583 | B2 | 8/2005 | Weinberg et al. |
| 6,937,903 | B2 | 8/2005 | Schuler et al. |
| 6,961,618 | B2 | 11/2005 | Osorio et al. |
| 6,978,787 | B1 | 12/2005 | Broniatowski |
| 7,011,638 | B2 | 3/2006 | Schuler et al. |
| 7,054,686 | B2 | 5/2006 | MacDonald |
| 7,054,692 | B1 | 5/2006 | Whitehurst et al. |
| 7,058,447 | B2 | 6/2006 | Hill et al. |
| 7,062,320 | B2 | 6/2006 | Ehlinger, Jr. |
| 7,069,082 | B2 | 6/2006 | Lindenthaler |
| 7,072,720 | B2 | 7/2006 | Puskas |
| 7,076,307 | B2 | 7/2006 | Boveja et al. |
| 7,142,910 | B2 | 11/2006 | Puskas |
| 7,142,917 | B2 | 11/2006 | Fukui |
| 7,149,574 | B2 | 12/2006 | Yun et al. |
| 7,155,279 | B2 | 12/2006 | Whitehurst et al. |
| 7,155,284 | B1 | 12/2006 | Whitehurst et al. |
| 7,167,750 | B2 | 1/2007 | Knudson et al. |
| 7,167,751 | B1 | 1/2007 | Whitehurst et al. |
| 7,174,218 | B1 | 2/2007 | Kuzma |
| 7,184,828 | B2 | 2/2007 | Hill et al. |
| 7,184,829 | B2 | 2/2007 | Hill et al. |
| 7,191,012 | B2 | 3/2007 | Boveja et al. |
| 7,204,815 | B2 | 4/2007 | Connor |
| 7,209,787 | B2 | 4/2007 | DiLorenzo |
| 7,225,019 | B2 | 5/2007 | Jahns et al. |
| 7,228,167 | B2 | 6/2007 | Kara et al. |
| 7,238,715 | B2 | 7/2007 | Tracey et al. |
| 7,242,984 | B2 | 7/2007 | DiLorenzo |
| 7,269,457 | B2 | 9/2007 | Shafer et al. |
| 7,345,178 | B2 | 3/2008 | Nunes et al. |
| 7,373,204 | B2 | 5/2008 | Gelfand et al. |
| 7,389,145 | B2 | 6/2008 | Kilgore et al. |
| 7,454,245 | B2 | 11/2008 | Armstrong et al. |
| 7,467,016 | B2 | 12/2008 | Colborn |
| 7,544,497 | B2 | 6/2009 | Sinclair et al. |
| 7,561,918 | B2 | 7/2009 | Armstrong et al. |
| 7,634,315 | B2 | 12/2009 | Cholette |
| 7,711,432 | B2 | 5/2010 | Thimineur et al. |
| 7,729,760 | B2 | 6/2010 | Patel et al. |
| 7,751,891 | B2 | 7/2010 | Armstrong et al. |
| 7,776,326 | B2 | 8/2010 | Milbrandt et al. |
| 7,797,058 | B2 | 9/2010 | Mrva et al. |
| 7,819,883 | B2 | 10/2010 | Westlund et al. |
| 7,822,486 | B2 | 10/2010 | Foster et al. |
| 7,829,556 | B2 | 11/2010 | Bemis et al. |
| 7,869,869 | B1 | 1/2011 | Farazi |
| 7,869,885 | B2 | 1/2011 | Begnaud et al. |
| 7,937,145 | B2 | 5/2011 | Dobak |
| 7,962,220 | B2 | 6/2011 | Kolafa et al. |
| 7,974,701 | B2 | 7/2011 | Armstrong |
| 7,974,707 | B2 | 7/2011 | Inman |
| 7,996,088 | B2 | 8/2011 | Marrosu et al. |
| 7,996,092 | B2 | 8/2011 | Mrva et al. |
| 8,019,419 | B1 | 9/2011 | Panescu et al. |
| 8,060,208 | B2 | 11/2011 | Kilgore et al. |
| 8,103,349 | B2 | 1/2012 | Donders et al. |
| 8,165,668 | B2 | 4/2012 | Dacey, Jr. et al. |
| 8,180,446 | B2 | 5/2012 | Dacey, Jr. et al. |
| 8,180,447 | B2 | 5/2012 | Dacey et al. |
| 8,195,287 | B2 | 6/2012 | Dacey, Jr. et al. |

(56) References Cited

U.S. PATENT DOCUMENTS

| | | | |
|---|---|---|---|
| 8,214,056 | B2 | 7/2012 | Hoffer et al. |
| 8,233,982 | B2 | 7/2012 | Libbus |
| 8,391,970 | B2 * | 3/2013 | Tracey ............... A61N 1/36053 607/2 |
| 8,412,338 | B2 * | 4/2013 | Faltys ............... A61N 1/36135 607/50 |
| 8,504,161 | B1 | 8/2013 | Kornet et al. |
| 8,571,654 | B2 | 10/2013 | Libbus et al. |
| 8,577,458 | B1 | 11/2013 | Libbus et al. |
| 8,600,505 | B2 | 12/2013 | Libbus et al. |
| 8,612,002 | B2 | 12/2013 | Faltys et al. |
| 8,630,709 | B2 | 1/2014 | Libbus et al. |
| 8,688,212 | B2 | 4/2014 | Libbus et al. |
| 8,700,150 | B2 | 4/2014 | Libbus et al. |
| 8,729,129 | B2 | 5/2014 | Tracey et al. |
| 8,788,034 | B2 | 7/2014 | Levine et al. |
| 8,843,210 | B2 | 9/2014 | Simon et al. |
| 8,855,767 | B2 | 10/2014 | Faltys et al. |
| 8,886,339 | B2 | 11/2014 | Faltys et al. |
| 8,914,114 | B2 | 12/2014 | Tracey et al. |
| 8,918,178 | B2 | 12/2014 | Simon et al. |
| 8,918,191 | B2 | 12/2014 | Libbus et al. |
| 8,923,964 | B2 | 12/2014 | Libbus et al. |
| 8,983,628 | B2 | 3/2015 | Simon et al. |
| 8,983,629 | B2 | 3/2015 | Simon et al. |
| 8,996,116 | B2 | 3/2015 | Faltys et al. |
| 9,114,262 | B2 | 8/2015 | Libbus et al. |
| 9,162,064 | B2 | 10/2015 | Faltys et al. |
| 9,174,041 | B2 | 11/2015 | Faltys et al. |
| 9,211,409 | B2 | 12/2015 | Tracey et al. |
| 9,211,410 | B2 | 12/2015 | Levine et al. |
| 9,254,383 | B2 | 2/2016 | Simon et al. |
| 9,272,143 | B2 | 3/2016 | Libbus et al. |
| 9,358,381 | B2 | 6/2016 | Simon et al. |
| 9,399,134 | B2 | 7/2016 | Simon et al. |
| 9,403,001 | B2 | 8/2016 | Simon et al. |
| 9,409,024 | B2 | 8/2016 | KenKnight et al. |
| 9,415,224 | B2 | 8/2016 | Libbus et al. |
| 9,452,290 | B2 | 9/2016 | Libbus et al. |
| 9,504,832 | B2 | 11/2016 | Libbus et al. |
| 9,511,228 | B2 | 12/2016 | Amurthur et al. |
| 9,533,153 | B2 | 1/2017 | Libbus et al. |
| 9,572,983 | B2 | 2/2017 | Levine et al. |
| 9,662,490 | B2 | 5/2017 | Tracey et al. |
| 9,700,716 | B2 | 7/2017 | Faltys et al. |
| 9,833,621 | B2 | 12/2017 | Levine |
| 9,849,286 | B2 | 12/2017 | Levine et al. |
| 9,987,492 | B2 | 6/2018 | Tracey et al. |
| 9,993,651 | B2 | 6/2018 | Faltys et al. |
| 2001/0002441 | A1 | 5/2001 | Boveja |
| 2001/0034542 | A1 | 10/2001 | Mann |
| 2002/0026141 | A1 | 2/2002 | Houben et al. |
| 2002/0040035 | A1 | 4/2002 | Myers et al. |
| 2002/0077675 | A1 | 6/2002 | Greenstein |
| 2002/0086871 | A1 | 7/2002 | O'Neill et al. |
| 2002/0095139 | A1 | 7/2002 | Keogh et al. |
| 2002/0099417 | A1 | 7/2002 | Naritoku et al. |
| 2002/0138075 | A1 | 9/2002 | Edwards et al. |
| 2002/0138109 | A1 | 9/2002 | Keogh et al. |
| 2002/0193859 | A1 | 12/2002 | Schulman et al. |
| 2002/0198570 | A1 | 12/2002 | Puskas |
| 2003/0018367 | A1 | 1/2003 | DiLorenzo |
| 2003/0032852 | A1 | 2/2003 | Perreault et al. |
| 2003/0045909 | A1 | 3/2003 | Gross et al. |
| 2003/0088301 | A1 | 5/2003 | King |
| 2003/0191404 | A1 | 10/2003 | Klein |
| 2003/0194752 | A1 | 10/2003 | Anderson et al. |
| 2003/0195578 | A1 | 10/2003 | Perron et al. |
| 2003/0212440 | A1 | 11/2003 | Boveja |
| 2003/0229380 | A1 | 12/2003 | Adams et al. |
| 2003/0236557 | A1 | 12/2003 | Whitehurst et al. |
| 2003/0236558 | A1 | 12/2003 | Whitehurst et al. |
| 2004/0002546 | A1 | 1/2004 | Altschuler |
| 2004/0015202 | A1 | 1/2004 | Chandler et al. |
| 2004/0015204 | A1 | 1/2004 | Whitehurst et al. |
| 2004/0015205 | A1 | 1/2004 | Whitehurst et al. |
| 2004/0024422 | A1 | 2/2004 | Hill et al. |
| 2004/0024428 | A1 | 2/2004 | Barrett et al. |
| 2004/0024439 | A1 | 2/2004 | Riso |
| 2004/0030362 | A1 | 2/2004 | Hill et al. |
| 2004/0039427 | A1 | 2/2004 | Barrett et al. |
| 2004/0048795 | A1 | 3/2004 | Ivanova et al. |
| 2004/0049121 | A1 | 3/2004 | Yaron |
| 2004/0049240 | A1 | 3/2004 | Gerber et al. |
| 2004/0059383 | A1 | 3/2004 | Puskas |
| 2004/0111139 | A1 | 6/2004 | McCreery et al. |
| 2004/0138517 | A1 | 7/2004 | Osorio et al. |
| 2004/0138518 | A1 | 7/2004 | Rise et al. |
| 2004/0138536 | A1 | 7/2004 | Frei et al. |
| 2004/0146949 | A1 | 7/2004 | Tan et al. |
| 2004/0153127 | A1 | 8/2004 | Gordon et al. |
| 2004/0158119 | A1 | 8/2004 | Osorio et al. |
| 2004/0162584 | A1 | 8/2004 | Hill et al. |
| 2004/0172074 | A1 | 9/2004 | Yoshihito |
| 2004/0172085 | A1 | 9/2004 | Knudson et al. |
| 2004/0172086 | A1 | 9/2004 | Knudson et al. |
| 2004/0172088 | A1 | 9/2004 | Knudson et al. |
| 2004/0172094 | A1 | 9/2004 | Cohen et al. |
| 2004/0176812 | A1 | 9/2004 | Knudson et al. |
| 2004/0178706 | A1 | 9/2004 | D'Orso |
| 2004/0193231 | A1 | 9/2004 | David et al. |
| 2004/0199209 | A1 | 10/2004 | Hill et al. |
| 2004/0199210 | A1 | 10/2004 | Shelchuk |
| 2004/0204355 | A1 | 10/2004 | Tracey et al. |
| 2004/0215272 | A1 | 10/2004 | Haubrich et al. |
| 2004/0215287 | A1 | 10/2004 | Swoyer et al. |
| 2004/0236381 | A1 | 11/2004 | Dinsmoor et al. |
| 2004/0236382 | A1 | 11/2004 | Dinsmoor et al. |
| 2004/0240691 | A1 | 12/2004 | Grafenberg |
| 2004/0243182 | A1 | 12/2004 | Cohen et al. |
| 2004/0243211 | A1 | 12/2004 | Colliou et al. |
| 2004/0254612 | A1 | 12/2004 | Ezra et al. |
| 2004/0267152 | A1 | 12/2004 | Pineda |
| 2005/0021092 | A1 | 1/2005 | Yun et al. |
| 2005/0021101 | A1 | 1/2005 | Chen et al. |
| 2005/0027328 | A1 | 2/2005 | Greenstein |
| 2005/0043774 | A1 | 2/2005 | Devlin et al. |
| 2005/0049655 | A1 | 3/2005 | Boveja et al. |
| 2005/0065553 | A1 | 3/2005 | Ben Ezra et al. |
| 2005/0065573 | A1 | 3/2005 | Rezai |
| 2005/0065575 | A1 | 3/2005 | Dobak |
| 2005/0070970 | A1 | 3/2005 | Knudson et al. |
| 2005/0070974 | A1 | 3/2005 | Knudson et al. |
| 2005/0075701 | A1 | 4/2005 | Shafer |
| 2005/0075702 | A1 | 4/2005 | Shafer |
| 2005/0095246 | A1 | 5/2005 | Shafer |
| 2005/0096707 | A1 | 5/2005 | Hill et al. |
| 2005/0103351 | A1 | 5/2005 | Stomberg et al. |
| 2005/0113894 | A1 | 5/2005 | Zilberman et al. |
| 2005/0131467 | A1 | 6/2005 | Boveja |
| 2005/0131486 | A1 | 6/2005 | Boveja et al. |
| 2005/0131487 | A1 | 6/2005 | Boveja |
| 2005/0131493 | A1 | 6/2005 | Boveja et al. |
| 2005/0137644 | A1 | 6/2005 | Boveja et al. |
| 2005/0137645 | A1 | 6/2005 | Voipio et al. |
| 2005/0143781 | A1 | 6/2005 | Carbunaru et al. |
| 2005/0143787 | A1 | 6/2005 | Boveja et al. |
| 2005/0149126 | A1 | 7/2005 | Libbus |
| 2005/0149129 | A1 | 7/2005 | Libbus et al. |
| 2005/0149131 | A1 | 7/2005 | Libbus et al. |
| 2005/0153885 | A1 | 7/2005 | Yun et al. |
| 2005/0154425 | A1 | 7/2005 | Boveja et al. |
| 2005/0154426 | A1 | 7/2005 | Boveja et al. |
| 2005/0165458 | A1 | 7/2005 | Boveja et al. |
| 2005/0177200 | A1 | 8/2005 | George et al. |
| 2005/0182288 | A1 | 8/2005 | Zabara |
| 2005/0182467 | A1 | 8/2005 | Hunter et al. |
| 2005/0187584 | A1 | 8/2005 | Denker et al. |
| 2005/0187586 | A1 | 8/2005 | David et al. |
| 2005/0187590 | A1 | 8/2005 | Boveja et al. |
| 2005/0191661 | A1 | 9/2005 | Gatanaga et al. |
| 2005/0192644 | A1 | 9/2005 | Boveja et al. |
| 2005/0197600 | A1 | 9/2005 | Schuler et al. |
| 2005/0197675 | A1 | 9/2005 | David et al. |

(56) References Cited

U.S. PATENT DOCUMENTS

| | | |
|---|---|---|
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0277912 A1 | 12/2005 | John |
| 2005/0282906 A1* | 12/2005 | Tracey .............. A61K 31/4747 514/614 |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0136024 A1 | 6/2006 | Cohen et al. |
| 2006/0142802 A1 | 6/2006 | Armstrong |
| 2006/0142822 A1 | 6/2006 | Tulgar |
| 2006/0149337 A1 | 7/2006 | John |
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178703 A1 | 8/2006 | Huston et al. |
| 2006/0178706 A1 | 8/2006 | Lisogurski et al. |
| 2006/0190044 A1 | 8/2006 | Libbus et al. |
| 2006/0190053 A1 | 8/2006 | Dobak |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241697 A1 | 10/2006 | Libbus et al. |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0136098 A1 | 6/2007 | Smythe et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0015659 A1 | 1/2008 | Zhang |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0051852 A1 | 2/2008 | Dietrich et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0166348 A1 | 7/2008 | Kupper et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0213331 A1 | 9/2008 | Gelfand et al. |

(56) References Cited

U.S. PATENT DOCUMENTS

| | | |
|---|---|---|
| 2008/0234780 A1 | 9/2008 | Smith |
| 2008/0234790 A1 | 9/2008 | Bayer et al. |
| 2008/0281197 A1 | 11/2008 | Wiley et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0062874 A1* | 3/2009 | Tracey ............ A61H 39/007 607/2 |
| 2009/0076561 A1 | 3/2009 | Libbus et al. |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0112291 A1 | 4/2009 | Wahlstrand et al. |
| 2009/0123521 A1 | 5/2009 | Weber et al. |
| 2009/0125076 A1* | 5/2009 | Shuros ............ A61N 1/36114 607/17 |
| 2009/0125079 A1 | 5/2009 | Armstrong et al. |
| 2009/0131995 A1 | 5/2009 | Sloan et al. |
| 2009/0143831 A1 | 6/2009 | Huston et al. |
| 2009/0171405 A1 | 7/2009 | Craig |
| 2009/0177112 A1 | 7/2009 | Gharib et al. |
| 2009/0187231 A1 | 7/2009 | Errico et al. |
| 2009/0210042 A1 | 8/2009 | Kowalczewski |
| 2009/0248097 A1 | 10/2009 | Tracey et al. |
| 2009/0254143 A1 | 10/2009 | Tweden et al. |
| 2009/0275997 A1* | 11/2009 | Faltys ............ A61N 1/056 607/2 |
| 2009/0276019 A1 | 11/2009 | Perez et al. |
| 2009/0281593 A9 | 11/2009 | Errico et al. |
| 2009/0281594 A1 | 11/2009 | King et al. |
| 2009/0312817 A1 | 12/2009 | Hogle et al. |
| 2010/0003656 A1 | 1/2010 | Kilgard et al. |
| 2010/0010556 A1 | 1/2010 | Zhao et al. |
| 2010/0010571 A1 | 1/2010 | Skelton et al. |
| 2010/0010581 A1 | 1/2010 | Goetz et al. |
| 2010/0010603 A1 | 1/2010 | Ben-David et al. |
| 2010/0016746 A1 | 1/2010 | Hampton et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0167937 A1* | 7/2010 | Goldknopf ......... G01N 33/6896 436/71 |
| 2010/0191304 A1 | 7/2010 | Scott |
| 2010/0215632 A1 | 8/2010 | Boss et al. |
| 2010/0241183 A1 | 9/2010 | DiLorenzo |
| 2010/0241207 A1 | 9/2010 | Bluger |
| 2010/0249859 A1 | 9/2010 | DiLorenzo |
| 2010/0280500 A1 | 11/2010 | Skelton et al. |
| 2010/0280562 A1 | 11/2010 | Pi et al. |
| 2010/0280569 A1 | 11/2010 | Bobillier et al. |
| 2011/0004266 A1 | 1/2011 | Sharma |
| 2011/0009734 A1 | 1/2011 | Foley et al. |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0144717 A1 | 6/2011 | Burton et al. |
| 2011/0145588 A1 | 6/2011 | Stubbs et al. |
| 2011/0152967 A1* | 6/2011 | Simon ............ A61N 2/002 607/45 |
| 2011/0224749 A1 | 9/2011 | Ben-David et al. |
| 2011/0247620 A1 | 10/2011 | Armstrong et al. |
| 2011/0275927 A1 | 11/2011 | Wagner et al. |
| 2011/0301658 A1 | 12/2011 | Yoo et al. |
| 2011/0307027 A1 | 12/2011 | Sharma et al. |
| 2012/0053657 A1 | 3/2012 | Parker et al. |
| 2012/0065706 A1 | 3/2012 | Vallapureddy et al. |
| 2012/0179219 A1 | 7/2012 | Kisker et al. |
| 2012/0185009 A1 | 7/2012 | Kornet et al. |
| 2012/0185020 A1 | 7/2012 | Simon et al. |
| 2012/0290035 A1* | 11/2012 | Levine ............ A61N 1/36053 607/40 |
| 2012/0296176 A1* | 11/2012 | Herbst ............ A61B 5/4839 600/301 |
| 2012/0302821 A1 | 11/2012 | Burnett |
| 2013/0013016 A1 | 1/2013 | Diebold |
| 2013/0066392 A1 | 3/2013 | Simon et al. |
| 2013/0066395 A1 | 3/2013 | Simon et al. |
| 2013/0071390 A1* | 3/2013 | Stadheim ............ C07K 16/2863 435/69.6 |
| 2013/0150756 A1 | 6/2013 | Vitek et al. |
| 2013/0245718 A1 | 9/2013 | Birkholz et al. |
| 2013/0289385 A1 | 10/2013 | Lozano et al. |
| 2013/0317580 A1 | 11/2013 | Simon et al. |
| 2014/0046407 A1 | 2/2014 | Ben-Ezra et al. |
| 2014/0206945 A1 | 7/2014 | Liao |
| 2014/0213926 A1 | 7/2014 | Vaidyanathan |
| 2014/0257425 A1 | 9/2014 | Arcot-Krishnamurthy et al. |
| 2014/0277260 A1 | 9/2014 | Khalil et al. |
| 2014/0288551 A1* | 9/2014 | Bharmi ............ A61N 1/36139 606/41 |
| 2014/0324118 A1 | 10/2014 | Simon et al. |
| 2014/0330335 A1 | 11/2014 | Errico et al. |
| 2015/0018728 A1 | 1/2015 | Gross et al. |
| 2015/0100100 A1 | 4/2015 | Tracey et al. |
| 2015/0119956 A1 | 4/2015 | Libbus et al. |
| 2015/0133717 A1 | 5/2015 | Ghiron et al. |
| 2015/0180271 A1 | 6/2015 | Angara et al. |
| 2015/0196767 A1 | 7/2015 | Ahmed |
| 2015/0202446 A1 | 7/2015 | Franke et al. |
| 2015/0233904 A1* | 8/2015 | Nayak ............ G01N 33/6896 435/7.92 |
| 2015/0241447 A1 | 8/2015 | Zitnik et al. |
| 2016/0067497 A1 | 3/2016 | Levine et al. |
| 2016/0089540 A1 | 3/2016 | Bolea |
| 2016/0096016 A1* | 4/2016 | Tracey ............ A61N 1/36053 604/20 |
| 2016/0114165 A1 | 4/2016 | Levine et al. |
| 2016/0250097 A9 | 9/2016 | Tracey et al. |
| 2016/0331952 A1 | 11/2016 | Faltys et al. |
| 2016/0367808 A9 | 12/2016 | Simon et al. |
| 2017/0113044 A1 | 4/2017 | Levine et al. |
| 2017/0197076 A1 | 7/2017 | Faltys et al. |
| 2017/0202467 A1 | 7/2017 | Zitnik et al. |
| 2017/0203103 A1 | 7/2017 | Levine et al. |
| 2017/0209705 A1 | 7/2017 | Faltys et al. |
| 2017/0239484 A1 | 8/2017 | Ram Rakhyani et al. |
| 2017/0254818 A1* | 9/2017 | Haskins ............ G01N 33/6896 |
| 2017/0304613 A1 | 10/2017 | Faltys et al. |
| 2017/0304621 A1 | 10/2017 | Malbert et al. |
| 2017/0361093 A1 | 12/2017 | Yoo et al. |
| 2018/0001096 A1 | 1/2018 | Faltys et al. |
| 2018/0021217 A1 | 1/2018 | Tracey et al. |
| 2018/0021580 A1 | 1/2018 | Tracey et al. |
| 2018/0078769 A1 | 3/2018 | Dinsmoor et al. |
| 2018/0085578 A1 | 3/2018 | Rennaker, II et al. |
| 2018/0117320 A1 | 5/2018 | Levine et al. |
| 2018/0289970 A1 | 10/2018 | Faltys et al. |
| 2019/0010535 A1* | 1/2019 | Pujol Onofre ......... A61K 45/06 |
| 2019/0022389 A1 | 1/2019 | Leonhardt |
| 2019/0090358 A1 | 3/2019 | Aresta et al. |
| 2019/0111263 A1* | 4/2019 | Levine ............ A61N 1/36175 |
| 2019/0192847 A1 | 6/2019 | Faltys et al. |
| 2019/0290902 A1 | 9/2019 | Romero-Ortega et al. |
| 2020/0330760 A1 | 10/2020 | Levine et al. |
| 2020/0384259 A1 | 12/2020 | Chasensky et al. |
| 2022/0040483 A1 | 2/2022 | Levine et al. |
| 2022/0118257 A1 | 4/2022 | Huston et al. |
| 2022/0257941 A1 | 8/2022 | Levine et al. |
| 2022/0280797 A1 | 9/2022 | Faltys et al. |
| 2022/0362555 A1 | 11/2022 | Zitnik et al. |
| 2023/0019961 A1 | 1/2023 | Huston et al. |
| 2023/0144580 A1 | 5/2023 | Manogue |
| 2023/0158301 A1 | 5/2023 | Levine et al. |
| 2023/0241387 A1 | 8/2023 | Levine et al. |

FOREIGN PATENT DOCUMENTS

| | | |
|---|---|---|
| CN | 101578067 A | 11/2009 |
| CN | 101868280 A | 10/2010 |

(56) References Cited

FOREIGN PATENT DOCUMENTS

| | | |
|---|---|---|
| CN | 104220129 A | 12/2014 |
| DE | 2628045 A1 | 1/1977 |
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 2073896 B1 | 10/2011 |
| EP | 3470111 A1 | 4/2019 |
| GB | 04133 | 2/1910 |
| GB | 2073428 A | 10/1981 |
| JP | 2017502787 | 1/2017 |
| JP | 2019517830 | 6/2019 |
| KR | 20050039445 A | 4/2005 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO2004/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO2007/133718 A2 | 11/2007 |
| WO | WO2010/005482 A1 | 1/2010 |
| WO | WO2010/067360 A2 | 6/2010 |
| WO | WO2010/118035 A2 | 10/2010 |
| WO | WO-2015009907 A1 * 1/2015 ........... C12Q 1/6883 | |
| WO | WO2016/134197 A1 | 8/2016 |
| WO | WO2019/204884 A1 | 10/2019 |

OTHER PUBLICATIONS

US 11,745,017 B2, 09/2023, Zanos et al. (withdrawn)
Katsavos S, Anagnostouli M. Biomarkers in Multiple Sclerosis: An Up-to-Date Overview. Mult Scler Int. 2013;2013:340508. doi: 10.1155/2013/340508. Epub Jan. 22, 2013. PMID: 23401777; PMCID: PMC3564381 (Year: 2013).*
Jacob, Anu, et al. "Detrimental role of granulocyte-colony stimulating factor in neuromyelitis optica: clinical case and histological evidence." Multiple Sclerosis Journal 18.12 (2012): 1801-1803. (Year: 2012).*
Abraham, Coagulation abnormalities in acute lung injury and sepsis, Am. J. Respir. Cell Mol. Biol., vol. 22(4), pp. 401-404, Apr. 2000.
Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.
Anderson et al.; Reflex principles of immunological homeostasis; Annu. Rev. Immunol.; 30; pp. 313-335; Apr. 2012.
Antonica, A., et al., Vagal control of lymphocyte release from rat thymus, J. Auton. Nerv. Syst., vol. 48(3), pp. 187-197, Aug. 1994.
Asakura et al., Non-surgical therapy for ulcerative colitis, Nippon Geka Gakkai Zasshi, vol. 98, No. 4, pp. 431-437, Apr. 1997 (abstract only).
Beliavskaia et al.,"On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.
Ben-Noun et al.; Neck circumference as a simple screening measure for identifying overweight and obese patients; Obesity Research; vol. 9; No. 8; pp. 470-477; Aug. 8, 2001.
Benoist, et al., "Mast cells in autoimmune disease" Nature., vol. 420(19): pp. 875-878, Dec. 2002.

Benthem et al.; Parasympathetic inhibition of sympathetic neural activity to the pancreas; Am.J.Physiol Endocrinol.Metab; 280(2); pp. E378-E381; Feb. 2001.
Bernik et al., Vagus nerve stimulation attenuates cardiac TNF production in endotoxic shock, (supplemental to Shock, vol. 15, 2001, Injury, inflammation and sepsis: laboratory and clinical approaches, Shock, Abstracts, 24th Annual Conference on Shock, Marco Island, FL, Jun. 9-12, 2001), Abstract No. 81.
Bernik et al., Vagus nerve stimulation attenuates endotoxic shock and cardiac TNF production, 87th Clinical Congress of the American College of Surgeons, New Orleans, LA, Oct. 9, 2001.
Bernik et al., Vagus nerve stimulation attenuates LPS-induced cardiac TNF production and myocardial depression in shock, New York Surgical Society, New York, NY, Apr. 11, 2001.
Bernik, et al., Pharmacological stimulation of the cholinergic antiinflammatory pathway, The Journal of Experimental Medicine, vol. 195, No. 6, pp. 781-788, Mar. 18, 2002.
Besedovsky, H., et al., Immunoregulatory feedback between interleukin-1 and glucocorticoid hormones, Science, vol. 233, No. 4764, pp. 652-654, Aug. 1986.
Bhattacharya, S.K. et al., Central muscarinic receptor subtypes and carrageenin-induced paw oedema in rats, Res. Esp. Med. vol. 191(1), pp. 65-76, Dec. 1991.
Bianchi et al., Suppression of proinflammatory cytokines in monocytes by a tetravalent guanylhydrazone, Journal of Experimental Medicine, vol. 183, pp. 927-936, Mar. 1996.
Biggio et al.; Chronic vagus nerve stimulation induces neuronal plasticity in the rat hippocampus; Int. J. Neurpsychopharmacol.; vol. 12; No. 9; pp. 1209-1221; Oct. 2009.
Blackwell, T. S. et al., Sepsis and cytokines: current status, Br. J. Anaesth., vol. 77(1), pp. 110-117, Jul. 1996.
Blum, A. et al., Role of cytokines in heart failure, Am. Heart J., vol. 135(2), pp. 181-186, Feb. 1998.
Boldyreff, Gastric and intestinal mucus, its properties and physiological importance, Acta Medica Scandinavica (journal), vol. 89, Issue 1-2, pp. 1-14, Jan./Dec. 1936.
Borovikova et al., Acetylcholine inhibition of immune response to bacterial endotoxin in human macrophages, Abstracts, Society for Neuroscience, 29th Annual Meeting, Miami Beach, FL, (Abs. No. 624.6); Oct. 23-28, 1999.
Borovikova et al., Efferent vagus nerve activity attenuates cytokine-mediated inflammation, Society for Neuroscience Abstracts, vol. 26, No. 102, Nov. 4-9, 2000 (abstract only).
Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.
Borovikova et al., Role of the efferent vagus nerve signaling in the regulation of the innate immune response to LPS, (supplemental to Shock, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.
Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).
Borovikova et al., Vagotomy blocks the protective effects of I.C.V. CNI-1493 against LPS-induced shock, (Supplemental to Shock, vol. 11, 1999, Molecular, cellular, and systemic pathobioloigal aspects and therapeutic approaches, abstacts and program, Fourth International Shock Congress and 22nd Annual Conference on Shock, Philadelphia, PA, Jun. 12-16, 1999), Abstract No. 277.
Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.
Borovikova, L. V., et al., Vagus nerve stimulation attenuates the systemic inflammatory response to endotoxin, Nature, vol. 405, No. 6785: pp. 458-462, May 25, 2000.
Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.

(56) References Cited

OTHER PUBLICATIONS

Bulloch et al.; Characterization of choline O-acetyltransferase (ChAT) in the BALB/C mouse spleen; Int.J.Neurosci.; 76(1-2); pp. 141-149; May 1994.

Bumgardner, G. L. et al., Transplantation and cytokines, Seminars in Liver Disease, vol. 19, No. 2, Thieme Medical Publishers; pp. 189-204, © 1999.

Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.

Bushby et al; Centiles for adult head circumference; Archives of Disease in Childhood; vol. 67(10); pp. 1286-1287; Oct. 1992.

Cano et al.; Characterization of the central nervous system innervation of the rat spleen using viral transneuronal tracing; J.Comp Neurol.; 439(1); pp. 1-18; Oct. 2001.

Carteron, N. L., Cytokines in rheumatoid arthritis: trials and tribulations, Mol. Med. Today, vol. 6(8), pp. 315-323, Aug. 2000.

Cavaillon et al.; The pro-inflammatory cytokine casade; Immune Response in the Critically Ill; Springer-Verlag Berlin Hiedelberg; pp. 37-66; Jan. 21, 2002.

Cheyuo et al.; The parasympathetic nervous system in the quest for stroke therapeutics; J. Cereb. Blood Flow Metab.; 31(5); pp. 1187-1195; May 2011.

Cicala et al., "Linkage between inflammation and coagulation: An update on the molecular basis of the crosstalk," Life Sciences, vol. 62(20); pp. 1817-1824, Apr. 1998.

Clark et al.; Enhanced recognition memory following vagus nerve stimulation in human subjects; Nat. Neurosci.; 2(1); pp. 94-98; Jan. 1999.

Cohen, "The immunopathogenesis of sepsis," Nature., vol. 420(6917): pp. 885-891, Dec. 2002.

Corcoran, et al., The effects of vagus nerve stimulation on pro- and anti-inflammatory cytokines in humans: a preliminary report, NeuroImmunoModulation, vol. 12(5), pp. 307-309, Sep. 2005.

Dake; Chronic cerebrospinal venous insufficiency and multiple sclerosis: Hostory and background; Techniques Vasc. Intervent. Radiol.; 15(2); pp. 94-100; Jun. 2012.

Das, Critical advances in spticemia and septic shock, Critical Care, vol. 4, pp. 290-296, Sep. 7, 2000.

Del Signore et al; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.

Diamond et al.; Mapping the immunological homunculus; Proc. Natl. Acad. Sci. USA; 108(9); pp. 3461-3462; Mar. 1, 2011.

Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.

Dinarello, C. A., The interleukin-1 family: 10 years of discovery, FASEB J., vol. 8, No. 15, pp. 1314-1325, Dec. 1994.

Dorr et al.; Effect of vagus nerve stimulation on serotonergic and noradrenergic transmission; J. Pharmacol. Exp. Ther.; 318(2); pp. 890-898; Aug. 2006.

Doshi et al., Evolving role of tissue factor and its pathway inhibitor, Crit. Care Med., vol. 30, suppl. 5, pp. S241-S250, May 2002.

Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.

Ellington et al., In vitro selection of RNA molecules that bind specific ligands, Nature, vol. 346, pp. 818-822, Aug. 30, 1990.

Ellrich et al.; Transcutaneous vagus nerve stimulation; Eur. Neurological Rev.; 6(4); pp. 254-256; Winter 2011.

Engineer et al.; Directing neural plasticity to understand and treat tinnitus; Hear. Res.; 295; pp. 58-66; Jan. 2013.

Engineer et al.; Reversing pathological neural activity using targeted plasticity; Nature; 470(7332); pp. 101-104; Feb. 3, 2011 (Author Manuscript).

Esmon, The protein C pathway, Crit. Care Med., vol. 28, suppl. 9, pp. S44-S48, Sep. 2000.

Fields; New culprits in chronic pain; Scientific American; pp. 50-57; Nov. 2009.

Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.

Fox, D. A., Cytokine blockade as a new strategy to treat rheumatoid arthritis, Arch. Intern. Med., vol. 160, pp. 437-444, Feb. 28, 2000.

Fox, et al., Use of muscarinic agonists in the treatment of Sjorgren' syndrome, Clin. Immunol., vol. 101, No. 3; pp. 249-263, Dec. 2001.

Fujii et al.; Simvastatin regulates non-neuronal cholinergic activity in T lymphocytes via CD11a-mediated pathways; J. Neuroimmunol.; 179(1-2); pp. 101-107; Oct. 2006.

Gao et al.; Investigation of specificity of auricular acupuncture points in regulation of autonomic function in anesthetized rats; Autonomic Neurosc.; 138(1-2); pp. 50-56; Feb. 29, 2008.

Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.

Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.

Ghelardini et al., S-(-)-ET 126: A potent and selective M1 antagonist in vitro and in vivo, Life Sciences, vol. 58, No. 12, pp. 991-1000, Feb. 1996.

Ghia, et al., The vagus nerve: a tonic inhibitory influence associated with inflammatory bowel disease in a murine model, Gastroenterology, vol. 131, No. 4, pp. 1122-1130, Oct. 2006.

Giebelen, et al., Stimulation of ?7 cholinergic receptors inhibits lipopolysaccharide-induced neutrophil recruitment by a tumor necrosis factor ?- independent mechanism, Shock, vol. 27, No. 4, pp. 443-447, Apr. 2007.

Goyal et al., Nature of the vagal inhibitory innervation to the lower esophageal sphincter, Journal of Clinical Investigation, vol. 55, pp. 1119-1126, May 1975.

Gracie, J. A., et al., A proinflammatory role for IL-18 in rheumatoid arthritis, J. Clin. Invest., vol. 104, No. 10, pp. 1393-1401, Nov. 1999.

Granert et al., Suppression of macrophage activation with CNI-1493 increases survival in infant rats with systemic haemophilus influenzae infection, Infection and Immunity, vol. 68, No. 9, pp. 5329-5334, Sep. 2000.

Green et al., Feedback technique for deep relaxation, Psycophysiology, vol. 6, No. 3, pp. 371-377, Nov. 1969.

Gregory et al., Neutrophil-kupffer-cell interaction in host defenses to systemic infections, Immunology Today, vol. 19, No. 11, pp. 507-510, Nov. 1998.

Groves et al.; Recordings from the rat locus coeruleus during acute vagal nerve stimulation in the anaesthetised rat; Neuroscience Letters; 379(3); pp. 174-179; May 13, 2005.

Guarente, Leonard, Ph. D.; Sirtuins, Aging, and Medicine; N Engl J Med ; vol. 364:pp. 2235-2244; Jun. 2011.

Guslandi, M., Nicotine treatment for ulcerative colitis, Br. J. Clin. Pharmacol., vol. 48(4), pp. 481-484, Oct. 1999.

Hansson, E.; Could chronic pain and spread of pain sensation be induced and maintained by glial activation?. Acta Physiologica, vol. 187, Issue 1-2; pp. 321R327, May/Jun. 2006.

Harrison's Principles of Internal Medicine, 13th Ed., pp. 511-515 and 1433-1435, Mar. 1994.

Hatton et al.; Vagal nerve stimulation: overview and implications for anesthesiologists; Int'l Anesthesia Research Society; vol. 103; No. 5; pp. 1241-1249; Nov. 2006.

Hirano, T., Cytokine suppresive agent improves survival rate in rats with acute pancreatitis of closed duodenal loop, J. Surg. Res., vol. 81, No. 2, pp. 224-229, Feb. 1999.

Hirao et al., The limits of specificity: an experimental analysis with RNA aptamers to MS2 coat protein variants, Mol. Divers., vol. 4, No. 2, pp. 75-89, 1999 (Accepted Jan. 13, 1999).

Hoffer et al.; Implantable electrical and mechanical interfaces with nerve and muscle; Annals of Biomedical Engineering; vol. 8; pp. 351-360; Jul. 1980.

(56) References Cited

OTHER PUBLICATIONS

Holladay et al., Neuronal nicotinic acetylcholine receptors as targets for drug discovery, Journal of Medicinal Chemistry, 40(26), pp. 4169-4194, Dec. 1997.
Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.
Hsu, et al., Analysis of efficiency of magnetic stimulation, IEEE Trans. Biomed. Eng., vol. 50(11), pp. 1276-1285, Nov. 2003.
Hsu, H. Y., et al., Cytokine release of peripheral blood monocuclear cells in children with chronic hepatitis B virus infection, J. Pediatr. Gastroenterol., vol. 29, No. 5, pp. 540-545, Nov. 1999.
Hu, et al., The effect of norepinephrine on endotoxin-mediated macrophage activation, J. Neuroimmunol., vol. 31(1), pp. 35-42, Jan. 1991.
Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.
Huston et al.; Transcutaneous vagus nerve stimulation reduces serum high mobility group box 1 levels and improves survival in murine sepsis; Crit. Care Med.; 35(12); pp. 2762-2768; Dec. 2007.
Hutchinson et al.; Proinflammatory cytokines oppose opioid induced acute and chronic analgesia; Brain Behav Immun.; vol. 22; No. 8; pp. 1178-1189; Nov. 2008.
Ilton et al., "Differential expression of neutrophil adhesion molecules during coronary artery surgery with cardiopulmonary bypass" Journal of Thoracic and Cardiovascular Surgery, Mosby—Year Book, inc., St. Louis, Mo, US, pp. 930-937, Nov. 1, 1999.
Jaeger et al., The structure of HIV-1 reverse transcriptase complexed with an RNA pseudoknot inhibitor, The EMBO Journal, 17(15), pp. 4535-4542, Aug. 1998.
Jander, S. et al., Interleukin-18 is induced in acute inflammatory demyelinating polymeuropathy, J. Neuroimmunol., vol. 114, pp. 253-258, Mar. 2001.
Joshi et al., Potent inhibition of human immunodeficiency virus type 1 replection by template analog reverse transcriptase , J. Virol., 76(13), pp. 6545-6557, Jul. 2002.
Kawahara et al.; SIRT6 links histone H3 lysine 9 deacetylation to NF-kappaB-dependent gene expression and organismal life span.; Cell. ; vol. 136; No. 1; pp. 62-74; Jan. 2009.
Kalishevskaya et al. "The character of vagotomy-and atropin-induced hypercoagulation," Sechenov Physiological Journal of the USSR, 65(3): pp. 398-404, Mar. 1979.
Kalishevskaya et al.; Nervous regulation of the fluid state of the blood; Usp. Fiziol. Nauk;,vol. 13; No. 2; pp. 93-122; Apr.-Jun. 1982.
Kanai, T. et al., Interleukin-18 and Crohn's disease, Digestion, vol. 63, suppl. 1, pp. 37-42, (year of pub. sufficiently earlier than effective US filing date and any foreign priority date) 2001.
Katagiri, M., et al., Increased cytokine production by gastric mucosa in patients with helicobacter pylori infection, J. Clin, Gastroenterol., vol. 25, Suppl. 1, pp. S211-S214, 1997.
Kawashima, et al., Extraneuronal cholinergic system in lymphocytes, Pharmacology & Therapeutics, vol. 86, pp. 29-48, Apr. 2000.
Kees et al; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.
Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.
Khatun, S., et al., "Induction of hypercoagulability condition by chronic localized cold stress in rabbits," Thromb. and Haemost., 81(3): pp. 449-455, Mar. 1999.
Kimball, et al., Levamisole causes differential cytokine expression by elicited mouse peritoneal macrophases, Journal of Leukocyte Biology, vo. 52, No. 3, pp. 349-356, Sep. 1992 (abstract only).
Kimmings, A. N., et al., Systemic inflammatory response in acute cholangitis and after subsequent treatment, Eur. J. Surg., vol. 166, pp. 700-705, Sep. 2000.
Kirchner et al.; Left vagus nerve stimulation suppresses experimentally induced pain; Neurology; vol. 55; pp. 1167-1171; Oct. 2000.
Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.
Koopman et al.; Pilot study of stimulation of the cholinergic anti-inflammatory pathway with an implantable vagus nerve stimulation device in patients with rheumatoid arthritis; Arth. Rheum.; 64(10 suppl.); pp. S195; Oct. 2012.
Krarup et al; Conduction studies in peripheral cat nerve using implanted electrodes: I. methods and findings in controls; Muscle & Nerve; vol. 11; pp. 922-932; Sep. 1988.
Kudrjashov, et al. "Reflex nature of the physiological anticoagulating system," Nature, vol. 196(4855): pp. 647-649; Nov. 17, 1962.
Kumins, N. H., et al., Partial hepatectomy reduces the endotoxin-induced peak circulating level of tumor necrosis factor in rats, Shock, vol. 5, No. 5, pp. 385-388, May 1996.
Kuznik, "Role of the vascular wall in the process of hemostatis," Usp Sovrem Biol., vol. 75(1): pp. 61-85, (year of pub. sufficiently earlier than effective US filing date and any foreign priority date)1973.
Kuznik, et al., "Blood Coagulation in stimulation of the vagus nerve in cats," Biull. Eskp. Biol. Med., vol. 78(7): pp. 7-9, (year of pub. sufficiently earlier than effective US filing date and any foreign priority date) 1974.
Kuznik, et al., "Heart as an efferent regulator of the process of blood coagulation and fibrinolysis," Kardiologiia, vol. 13(3): pp. 10-17, (year of pub. sufficiently earlier than effective US filing date and any foreign priority date) 1973.
Kuznik, et al., "Role of the heart and vessels in regulating blood coagulation and fibrinolysis," Kagdiologiia, vol. 13(4): pp. 145-154, Apr. 1973.
Kuznik, et al., "Secretion of blood coagulation factors into saliva under conditions of hypo-and hypercoagulation," Voprosy Meditsinskoi Khimii, vol. 19(1): pp. 54-57; (year of pub. sufficiently earlier than effective US filing date and any foreign priority date) 1973.
Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.
Kuznik, et al., "The role of the vascular wall in the mechanism of control of blood coagulation and fibrinolysis on stimulation of the vagus nerve," Cor Vasa, vol. 17(2): pp. 151-158, (year of pub. sufficiently earlier than effective US filing date and any foreign priority date) 1975.
Lang, et al., "Neurogienic control of cerebral blood flow," Experimental Neurology, 43(1): pp. 143-161, Apr. 1974.
Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.
LeNovere, N. et al., Molecular evolution of the nicotinic acetylcholine receptor: an example of multigene family in excitable cells, J. Mol. Evol., 40, pp. 155-172, Feb. 1995.
Leonard, S. et al., Neuronal nicotinic receptors: from structure to function, Nicotine & Tobacco Res. 3:203-223, Aug. 2001.
Lips et al.; Coexpression and spatial association of nicotinic acetylcholine receptor subunits alpha7 and alpha10 in rat sympathetic neurons; J.Mol.Neurosci.; 30; pp. 15-16; Feb. 2006.
Lipton, J. M. et al.; Anti-inflammatory actions of the neuroimmunomodulator ?-MSH, Immunol. Today, vol. 18, pp. 140-145, Mar. 1997.
Loeb et al.; Cuff electrodes for chronic stimulation and recording of peripheral nerve activity; Journal of Neuroscience Methods; vol. 64; pp. 95-103; Jan. 1996.
Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.
Manta et al.; Optimization of vagus nerve stimulation parameters using the firing activity of serotonin neurons in the rat dorsal raphe;

(56) References Cited

OTHER PUBLICATIONS

European Neuropsychopharmacology; vol. 19; pp. 250-255; Jan. 2009 (doi: 10.1016/j.euroneuro.2008.12.001).
Martindale: The Extra Pharmacopoeia; 28th Ed. London; The Pharmaceutical Press; pp. 446-485; © 1982.
Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.
McGuinness, P. H., et al., Increases in intrahepatic CD68 positive cells, MAC387 positive cells, and proinflammatory cytokines (particulary interleukin 18) in chronic hepatitis C infection, Gut, vol. 46(2), pp. 260-269, Feb. 2000.
Miguel-Hidalgo, J.J.; The role of glial cells in drug abuse; Current Drug Abuse Reviews; vol. 2; No. 1; pp. 76-82; Jan. 2009.
Milligan et al.; Pathological and protective roles of glia in chronic pain; Nat Rev Neurosci.; vol. 10; No. 1; pp. 23-26; Jan. 2009.
Minnich et al.; Anti-cytokine and anti-inflammatory therapies for the treatment of severe sepsis: progress and pitfalls; Proceedings of the Nutrition Society; vol. 63(3); pp. 437-441; Aug. 2004.
Mishchenko, et al., "Coagulation of the blood and fibrinolysos in dogs during vagal stimulation," Sechenov Physiological Journal of the USSR, vol. 61(1): pp. 101-107, 1975.
Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.
Molina et al., CNI-1493 attenuates hemodynamic and proinflammatory responses to LPS, Shock, vol. 10, No. 5, pp. 329-334, Nov. 1998.
Nadol et al., "Surgery of the Ear and Temporal Bone," Lippinkott Williams & Wilkins, 2nd Ed., 2005, (Publication date: Sep. 21, 2004), p. 580.
Nagashima et al., Thrombin-activatable fibrinolysis inhibitor (TAFI) deficiency is compatible with murine life, J. Clin. Invest., 109, pp. 101-110, Jan. 2002.
Nathan, C. F., Secretory products of macrophages, J. Clin. Invest., vol. 79(2), pp. 319-326, Feb. 1987.
Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.
Navzer et al.; Reversing pathological neural activity using targeted plasticity; Nature; 470(7332); pp. 101-104; Feb. 3, 2011.
Neuhaus et al.; P300 is enhanced in responders to vagus nerve stimulation for treatment of major depressive disorder; J. Affect. Disord.; 100(1-3); pp. 123-128; Jun. 2007.
Noguchi et al., Increases in Gastric acidity in response to electroacupuncture stimulation of hindlimb of anesthetized rats, Jpn. J. Physiol., 46(1), pp. 53-58, Feb. 1996.
Norton, Can ultrasound be used to stimulate nerve tissue, BioMedical Engineering OnLine, 2(1), pp. 6, Mar. 4, 2003.
Olofsson et al.; Rethinking inflammation: neural circuits in the regulation of immunity; Immunological Reviews; 248(1); pp. 188-204; Jul. 2012.
Oshinsky et al.; Non-invasive vagus nerve stimulation as treatment for trigeminal allodynia; Pain; 155(5); pp. 1037-1042; May 2014.
Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.
Pateyuk, et al.,"Treatment of Botkin's disease with heparin," Klin. Med., vol. 51(3): pp. 113-117, Mar. 1973.
Pavlov et al.; Controlling inflammation: the cholinergic antiinflammatory pathway; Biochem. Soc. Trans.; 34(Pt 6); pp. 1037-1040; Dec. 2006.
Payne, J. B. et al., Nicotine effects on PGE2 and IL-1 beta release by LPS-treated human monocytes, J. Perio. Res., vol. 31, No. 2, pp. 99-104, Feb. 1996.
Peuker; The nerve supply of the human auricle; Clin. Anat.; 15(1); pp. 35-37; Jan. 2002.
Pongratz et al.; The sympathetic nervous response in inflammation; Arthritis Research and Therapy; 16(504); 12 pages; retrieved from the internet (http://arthritis-research.com/content/16/6/504) ; Jan. 2014.
Prystowsky, J. B. et al., Interleukin-1 mediates guinea pig gallbladder inflammation in vivo, J. Surg. Res., vol. 71, No. 2, pp. 123-126, Aug. 1997.
Pulkki, K. J., Cytokines and cardiomyocyte death, Ann. Med., vol. 29(4), pp. 339-343, Aug. 1997.
Pullan, R. D., et al., Transdermal nicotine for active ulceratiive colitis, N. Engl. J. Med., vol. 330, No. 12, pp. 811-815, Mar. 24, 1994.
Pulvirenti et al; Drug dependence as a disorder of neural plasticity:focus on dopamine and glutamate; Rev Neurosci.; vol. 12; No. 2; pp. 141-158; Apr./Jun. 2001.
Rahman et al.; Mammalian Sirt 1: Insights on its biological functions; Cell Communications and Signaling; vol. 9; No. 11; pp. 1-8; May 2011.
Rayner, S. A. et al., Local bioactive tumour necrosis factor (TNF) in corneal allotransplantation, Clin. Exp. Immunol., vol. 122, pp. 109-116, Oct. 2000.
Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.
Rinner et al.; Rat lymphocytes produce and secrete acetylcholine in dependence of differentiation and activation; J.Neuroimmunol.; 81(1-2); pp. 31-37; Jan. 1998.
Robinson et al.; Studies with the Electrocardiogram the Action of the Vagus Nerve on the Human Heart; J Exp Med; 14(3):217-234; Sep. 1911.
Romanovsky, A. A., et al., The vagus nerve in the thermoregulatory response to systemic inflammation, Am. J. Physiol., vol. 273, No. 1 (part 2), pp. R407-R413, Jul. 1, 1997.
Saghizadeh et al.; The expression of TNF? by human muscle; J. Clin. Invest.; vol. 97; No. 4; pp. 1111-1116; Feb. 15, 1996.
Saindon et al.; Effect of cervical vagotomy on sympathetic nerve responses to peripheral interleukin-1beta; Auton.Neuroscience Basic and Clinical; 87; pp. 243-248; Mar. 23, 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.
Sandborn, W. J., et al., Transdermal nicotine for mildly to moderately active ulcerative colitis, Ann. Intern. Med, vol. 126, No. 5, pp. 364-371, Mar. 1, 1997.
Sato, E., et al., Acetylcholine stimulates alveolar macrophages to release inflammatory cell chemotactic activity, Am. J. Physiol., vol. 274, pp. L970-L979, Jun. 1998.
Sato, K.Z., et al., Diversity of mRNA expression for muscarinic acetylcholine receptor subtypes and neuronal nicotinic acetylcholine receptor subunits in human mononuclear leukocytes and leukemic cell lines, Neuroscience Letters, vol. 266, pp. 17-20, Apr. 30, 1999.
Scheinman, R. I., et al., Role of transcriptional activation of I?B? in mediation of immunosuppression by glucocorticoids, Science, vol. 270, No. 5234, pp. 283-286, Oct. 13, 1995.
Schneider et al., High-affinity ssDNA inhibitors of the review transcriptase of type 1 human immunodeficiency virus, Biochemistry, 34(29), pp. 9599-9610, Jul. 1995.
Shafer, Genotypic testing for human immunodeficiency virus type 1 drug resistance, Clinical Microbiology Reviews, vol. 15, pp. 247-277, Apr. 2002.
Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.
Sher, M. E., et al., The influence of cigarette smoking on cytokine levels in patients with inflammatory bowel disease, Inflamm. Bowel Dis., vol. 5, No. 2, pp. 73-78, May 1999.
Shi et al.; Effects of efferent vagus nerve excitation on inflammatory response in heart tissue in rats with endotoxemia; vol. 15, No. 1; pp. 26-28; Jan. 2003 (Eng. Abstract).

(56) References Cited

OTHER PUBLICATIONS

Snyder et al., Correction of hemophilia B in canine and murine models using recombinant adeno-associated viral vectors; Nature Medicine, 5(1), pp. 64-70, Jan. 1999.
Sokratov, et al. "The role of choline and adrenegic structures in regulation of renal excretion of hemocoagulating compounds into the urine," Sechenov Physiological Journal of the USSR, vol. 63(12): pp. 1728-1732, 1977.
Stalcup et al., Endothelial cell functions in the hemodynamic responses to stress, Annals of the New York Academy of Sciences, vol. 401, pp. 117-131, Dec. 1982.
Steinlein, New functions for nicotine acetylcholine receptors?, Behavioural Brain Res., vol. 95(1), pp. 31-35, Sep. 1998.
Sternberg, E. M., Perspectives series: cytokines and the brain 'neural-immune interactions in health and disease,' J. Clin. Invest., vol. 100, No. 22, pp. 2641-2647, Dec. 1997.
Stevens et al.; The anti-inflammatory effect of some immunosuppressive agents; J. Path.; 97(2); pp. 367-373; Feb. 1969.
Strojnik et al.; Treatment of drop foot using and implantable peroneal underknee stimulator; Scand. J. Rehab. Med.; vol. 19(1); pp. 37R43; Dec. 1986.
Sugano et al., Nicotine inhibits the production of inflammatory mediators in U937 cells through modulation of nuclear factor-kappaβ activation, Biochemical and Biophysical Research Communications, vol. 252, No. 1, pp. 25-28, Nov. 9, 1998.
Suter et al.; Do glial cells control pain?; Neuron Glia Biol.; vol. 3; No. 3; pp. 255-268; Aug. 2007.
Swick et al.; Locus coeruleus neuronal activity in awake monkeys: relationship to auditory P300-like potentials and spontaneous EEG. Exp. Brain Res.; 101(1); pp. 86-92; Sep. 1994.
Sykes, et al., An investigation into the effect and mechanisms of action of nicotine in inflammatory bowel disease, Inflamm. Res., vol. 49, pp. 311-319, Jul. 2000.
Takeuchi et al., A comparison between chinese blended medicine "Shoseiryuto" tranilast and ketotifen on the anit-allergic action in the guinea pigs, Allergy, vol. 34, No. 6, pp. 387-393, Jun. 1985 (eng. abstract).
Tekdemir et al.; A clinico-anatomic study of the auricular branch of the vagus nerve and arnold's ear-cough reflex; Surg. Radiol. Anat.; 20(4); pp. 253-257; Mar. 1998.
Toyabe, et al., Identification of nicotinic acetylcholine receptors on lymphocytes in the periphery as well as thymus in mice, Immunology, vol. 92(2), pp. 201-205, Oct. 1997.
Tracey et al., Mind over immunity, Faseb Journal, vol. 15, No. 9, pp. 1575-1576, Jul. 2001.
Tracey, K. J. et al., Anti-cachectin/TNF monoclonal antibodies prevent septic shock during lethal bacteraemia; Nature, 330: pp. 662-664, Dec. 23, 1987.
Tracey, K. J. et al., Physiology and immunology of the cholinergic antiinflammatory pathway; J Clin Invest.; vol. 117: No. 2; pp. 289-296; Feb. 2007.
Tracey, K. J.; Reflex control of immunity; Nat Rev Immunol; 9(6); pp. 418-428; Jun. 2009.
Tracey, K. J. et al., Shock and tissue injury induced by recombinant human cachectin, Science, vol. 234, pp. 470-474, Oct. 24, 1986.
Tracey, K.J., The inflammatory reflex, Nature, vol. 420, pp. 853-859, Dec. 19-26, 2002.
Tsutsui, H., et al., Pathophysiolocical roles of interleukin-18 in inflammatory liver diseases; Immunol. Rev., 174:192-209, Apr. 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 DNA polymerase; Science, 249(4968), pp. 505-510, Aug. 3, 1990.
Van Dijk, A. P., et al., Transdermal nicotine inhibits interleukin 2 synthesis by mononuclear cells derived from healthy volunteers, Eur. J. Clin. Invest, vol. 28, pp. 664-671, Aug. 1998.
Van Der Horst et al.; Stressing the role of FoxO proteins in lifespan and disease; Nat Rev Mol Cell Biol.; vol. 8; No. 6; pp. 440-450; Jun. 2007.
Vanhoutte, et al., Muscarinic and beta-adrenergic prejunctional modulation of adrenergic neurotransmission in the blood vessel wall, Gen Pharmac., vol. 14(1), pp. 35-37, Jan. 1983.
VanWesterloo, et al., The cholinergic anti-inflammatory pathway regulates the host response during septic peritonitis, The Journal of Infectious Diseases, vol. 191, pp. 2138-2148, Jun. 15, 2005.
Ventureyra, Transcutaneous vagus nerve stimulation for partial onset seizure therapy, Child's Nerv Syst, vol. 16(2), pp. 101-102, Feb. 2000.
Vijayaraghavan, S.; Glial-neuronal interactions-implications for plasticity anddrug addictionl AAPS J.; vol. 11; No. 1; pp. 123-132; Mar. 2009.
Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.
Von Känel, et al., Effects of non-specific ?-adrenergic stimulation and blockade on blood coagulation in hypertension, J. Appl. Physiol., vol. 94, pp. 1455-1459, Apr. 2003.
Von Känel, et al., Effects of sympathetic activation by adrenergic infusions on hemostasis in vivo, Eur. J. Haematol., vol. 65: pp. 357-369, Dec. 2000.
Walland et al., Compensation of muscarinic brochial effects of talsaclidine by concomitant sympathetic activation in guinea pigs; European Journal of Pharmacology, vol. 330(2-3), pp. 213-219, Jul. 9, 1997.
Wang et al; Nicotinic acetylcholine receptor alpha7 subunit is an essential regulator of inflammation; Nature; 421; 384-388; Jan. 23, 2003.
Wang, H., et al., HMG-1 as a late mediator of endotoxin lethality in mice, Science, vol. 285, pp. 248-251, Jul. 9, 1999.
Waserman, S. et al., TNF-? dysregulation in asthma: relationship to ongoing corticosteroid therapy, Can. Respir. J., vol. 7, No. 3, pp. 229-237, May-Jun. 2000.
Watanabe, H. et al., The significance of tumor necrosis factor (TNF) levels for rejection of joint allograft, J. Reconstr. Microsurg., vol. 13, No. 3, pp. 193-197, Apr. 1997.
Wathey, J.C. et al., Numerical reconstruction of the quantal event at nicotinic synapses; Biophys. J., vol. 27: pp. 145-164, Jul. 1979.
Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.
Watkins, L.R. et al., Implications of immune-to-brain communication for sickness and pain, Proc. Natl. Acad. Sci. U.S.A., vol. 96(14), pp. 7710-7713, Jul. 6, 1999.
Webster's Dictionary, definition of "intrathecal", online version accessed Apr. 21, 2009.
Weiner, et al., "Inflammation and therapeutic vaccination in CNS diseases," Nature., vol. 420(6917): pp. 879-884, Dec. 19-26, 2002.
Westerheide et al.; Stress-inducible regulation of heat shock factor 1 by the deacetylase SIRT1.; Science; Vo. 323; No. 5717; pp. 1063-1066; Feb. 2009.
Whaley, K. et al., C2 synthesis by human monocytes is modulated by a nicotinic cholinergic receptor, Nature, vol. 293, pp. 580-582, Oct. 15, 1981.
Woiciechowsky, C. et al., Sympathetic activation triggers systemic interleukin-10 release in immunodepression induced by brain injury, Nature Med., vol. 4, No. 7, pp. 808-813, Jul. 1998.
Yeh, S.S. et al., Geriatric cachexia: the role of cytokines, Am. J. Clin. Nutr., vol. 70(2), pp. 183-197, Aug. 1999.
Yu et al.; Low-level transcutaneous electrical stimulation of the auricular branch of the vagus nerve: a non-invasive approach to treat the initial phase of atrial fibrillation; Heart Rhythm; 10(3); pp. 428-435; Mar. 2013.
Zamotrinsky et al.; Vagal neurostimulation in patients with coronary artery disease; Auton. Neurosci.; 88(1-2); pp. 109-116; Apr. 2001.
Zhang et al., Tumor necrosis factor, The Cytokine Handbook, 3rd ed., Ed. Thompson, Academic Press, pp. 517-548, Jul. 1, 1998.

(56) References Cited

OTHER PUBLICATIONS

Zhang et al.; Roles of SIRT1 in the acute and restorative phases following induction of inflammation.; J Biol Chem.; vol. 285; No. 53; pp. 41391-41401; Dec. 2010.

Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.

Zhao et al.; Transcutaneous auricular vagus stimulation protects endotoxemic rat from lipopolysaccharide-induced inflammation; Evid. Based Complement Alternat. Med.; vol. 2012; Article ID 627023; 10 pages; Dec. 29, 2012.

Levine et al.; U.S. Appl. No. 16/103,873 entitled "Vagus nerve stimulation pre-screening test," filed Aug. 14, 2018.

Zitnik et al.; U.S. Appl. No. 16/356,906 entitled "Batteryless Implantable Microstimulators," filed Mar. 18, 2019.

Faltys et al.; U.S. Appl. No. 16/544,805 entitled "Nerve cuff with pocket for leadless stimulator," filed Aug. 19, 2019.

Faltys et al.; U.S. Appl. No. 16/544,882 entitled "Neural stimulation devices and systems for treatment of chronic inflammation," filed Aug. 19, 2019.

Crusz et al.; Inflammation and cancer; advances and new agents; Nature reviews Clinical Oncology; 12(10); pp. 584-596; doi: 10.1038/nrclinonc.2015.105; Jun. 30, 2015.

Strowig et al.; Inflammasomes in health and disease; Nature; vol. 481; pp. 278-286; doi: 10.1038/nature10759; Jan. 19, 2012.

Manogue; U.S. Appl. No. 16/582,726 entitled "Methods and apparatuses for reducing bleeding via coordinated trigeminal and vagal nerve stimulation," filed Sep. 25, 2019.

Tracey et al., U.S. Appl. No. 16/231,581 entitled "Inhibition of inflammatory cytokine production by cholinergic agnostics and vagus nerve stimulation," filed Dec. 23, 2018.

Housley et al.; Biomarkers in multiple sclerosis; Clinical Immunology; 161(1); pp. 51-58; Nov. 2015.

Katsavos et al.; Biomarkers in multiple sclerosis: an up-to-date overview; Multiple Sclerosis International; vol. 2013, Article ID 340508, 20 pages; (year of pub. sufficiently earlier than effective US filing date and any foreign priority date) 2013.

Faltys et al.; U.S. Appl. No. 16/728,880 entitled "Implantable neurostimulator having power control and thermal regulation and methods of use," filed Dec. 27, 2019.

Faltys et al.; U.S. Appl. No. 16/785,400 entitled "Systems and methods for establishing a nerve block," filed Feb. 7, 2020.

Levine et al.; U.S. Appl. No. 17/337,292 entitled "Closed-loop vagus nerve stimulation," filed Jun. 2, 2021.

Tracey et al.; U.S. Appl. No. 17/170,772 entitled "Treatment of bleeding by non-invasive stimulation," filed Feb. 8, 2021.

Palov et al.; The cholinergic anti-inflammatory pathway: a missing link in neuroimmunomodulation; Molecular Medicine; 9(5); pp. 125-134; May 2003.

Caravaca et al.; A novel flexible cuff-like microelectrode for dual purpose, acute and chronic electrical interfacing with the mouse cervical vagus nerve; Journal of Neural Engineering; 14(6);066005; Nov. 1, 2017.

Koopman et al.; THU0237 first-in-human study of vagus nerve stimulation for rheumatoid arthritis: clinical and biomarker results through day 84; Annals of the Rheumatic Diseases; 72(Suppl 3):A245; Jun. 1, 2013 (Abstract Only).

Koopman et al.; Vagus nerve stimulation inhibits cytokine production and attenuates disease severity in rheumatoid arthritis; Proceedings of the National Academy of Sciences; 113(29); pp. 8284-8289; Jul. 19, 2016.

Mayo Clinic; The factsheet of vagus nerve stimulation from the Mayo Clinic website: www.mayoclinic.org/tests-procedures/vagus-nerve-sti mulation/about/pac-20384565; retrieved from the internet on Sep. 28, 2021.

Faltys et al.; U.S. Appl. No. 17/443,875 entitled "Neural stimulation devices and systems for treatment of chronic inflammation," filed Jul. 28, 2021.

Koopman et al.; Pilot study of stimulation of the cholinergic anti-inflammatory pathway with an implantable vagus nerve stimulation device in patients with rheumatoid arthritis; 2012 ACR/ARHP Annual Meeting; Abstract No. 451; 4 pages; retrieved from the internet (https://acrabstracts.org/abstract/pilot-study-of-stimulation-of-the-cholinergic-anti-inflammatory-pathway-with-an-implantable-vagus-nerve-stimulation-device-in-patients-with-rheumatoid-arthritis); (Abstract Only); on Sep. 24, 2020.

Pavlov et al.; The cholinergic anti-inflammatory pathway; Brain, Behavior, and Immunity; 19; p. 493-499; Nov. 2005.

Zitnik et al.; Treatment of chronic inflammatory diseases with implantable medical devices; Cleveland Clinic Journal of Medicine; 78(Suppl 1); pp. S30-S34; Aug. 2011.

Levine et al.; U.S. Appl. No. 17/599,594 entitled "Vagus nerve stimulation to treat neurodegenerative disorders," filed Sep. 29, 2021.

Manogue; U.S. Appl. No. 17/578,339 entitled "Methods and apparatuses for reducing bleeding via coordinated trigeminal and vagal nerve stimulation," filed Jan. 18, 2022.

Faltys et al.; U.S. Appl. No. 17/700,415 entitled "Systems and methods for establishing a nerve block," filed Mar. 21, 2022.

De Jonge et al.; Stimulation of the vagus nerve attenuates macrophage activation by activating the Jak2-STAT3 signaling pathway; Nature Immunology; 6(8); pp. 844-851; Aug. 2005.

Emery et al.; Rituximab versus an alternative TNF inhibitor in patients with rheumatoid arthritis who failed to respond to a single previous TNF inhibitor: switch-rа, a global, oberservational, comparative effectiveness study; Annals of the Rheumatic Diseases; 4(6); pp. 979-984; Jun. 2015.

Gottenberg et al.; Non-TNF-targeted biologic vs a second anti-TNF drug to treat rheumatoid arthritis in patients with insufficient response to a first anti TNF drug: a randomized clinical trial; JAMA; 316(11); pp. 1172-1180; Sep. 2016.

Monaco et al.; Anti-TNF therapy:past,present, and future; International Immunology; 27(1); pp. 55-62; Jan. 2015.

Olofsson et al.; Single-pulse and unidirectional electrical activation of the cervical vagus nerve reduces tumor necrosis factor in endotoxemia; Bioelectronic Medicine; 2(1); pp. 37-42; Jun. 2015.

Rendas-Baum et al.; Evaluating the efficacy of sequential biologic therapies for rheumatoid arthritis patients with an inadequate response to tumor necrosis factor—alpha inhibitors; Arthritis research and therapy; 13; R25; 15 pages; ; Feb. 2011.

Rosas-Ballina et al.; Acetylcholine-synthesizing T cells relay neural signals in a vagus nerve circuit Science: 334(6052); pp. 98-101; 10 pages; (Author Manuscript); Oct. 2011.

Vida et al.; Aplha 7-cholinergic receptor mediates vagal induction of splenic norepinephrine; Journal of Immunology; 186(7); pp. 4340-4346; 16 pages; (Author Manuscript); Apr. 2011.

Yang et al.; Acetylcholine inhibits LPS-induced MMP-9 production and ccell migration via the alpha7 nAChR-JAK2/STAT3 pathway in RAW264.7 cells; Cellular Physiology and Biochemistry: 36(5); pp. 2025-2038; (the year of publication is sufficiently earlier than the effective U.S. filing date and any foreign priority date so that the particular month of publication is not in issue) 2015.

Zanos et al.; U.S. Appl. No. 18/335,116 entitled "Systems and methods for vagus nerve stimulation," filed Jun. 14, 2023.

Yang et al.; Axon myelination and electrical stimulation in a microfluidic, compartmentalized cell culture platform; Neuromolecular medicine; vol. 14; pp. 112-118; Jun. 2012.

Gautron et al.; Neurobiology of inflammation-associated anorexia; Frontiers in Neuroscience; 3(59); 10 pages; Jan. 8, 2010.

Hebb et al.; Creating the Feedback Loop: Closed-Loop Neurostimulation; Neurosurgery Clinics of North America; 25(1); pp. 187-204; Jan. 28, 2014.

* cited by examiner

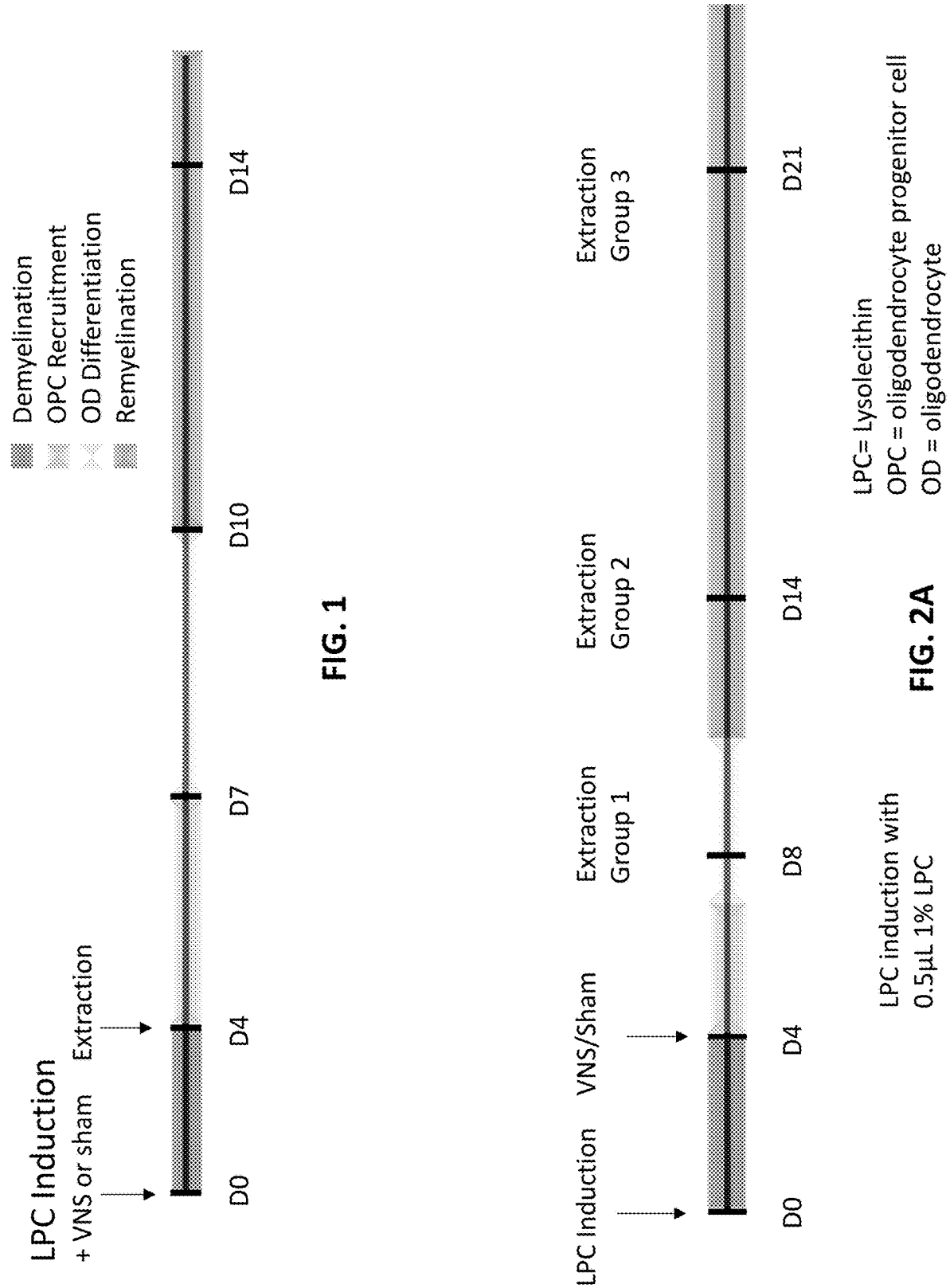

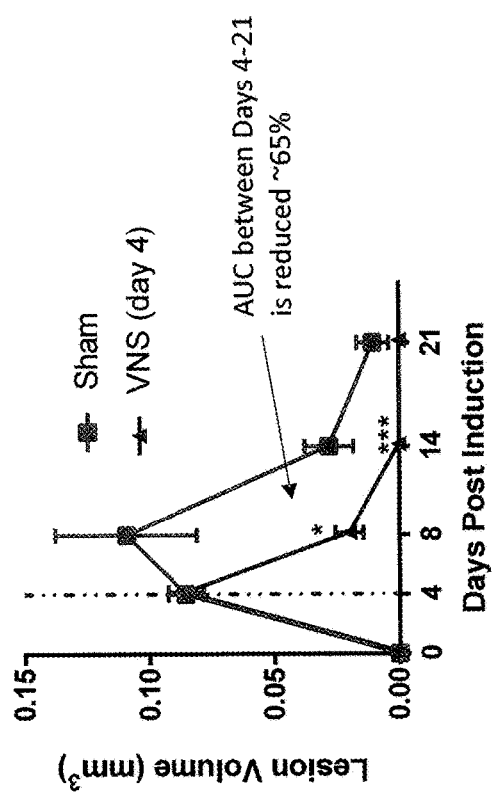
FIG. 5A
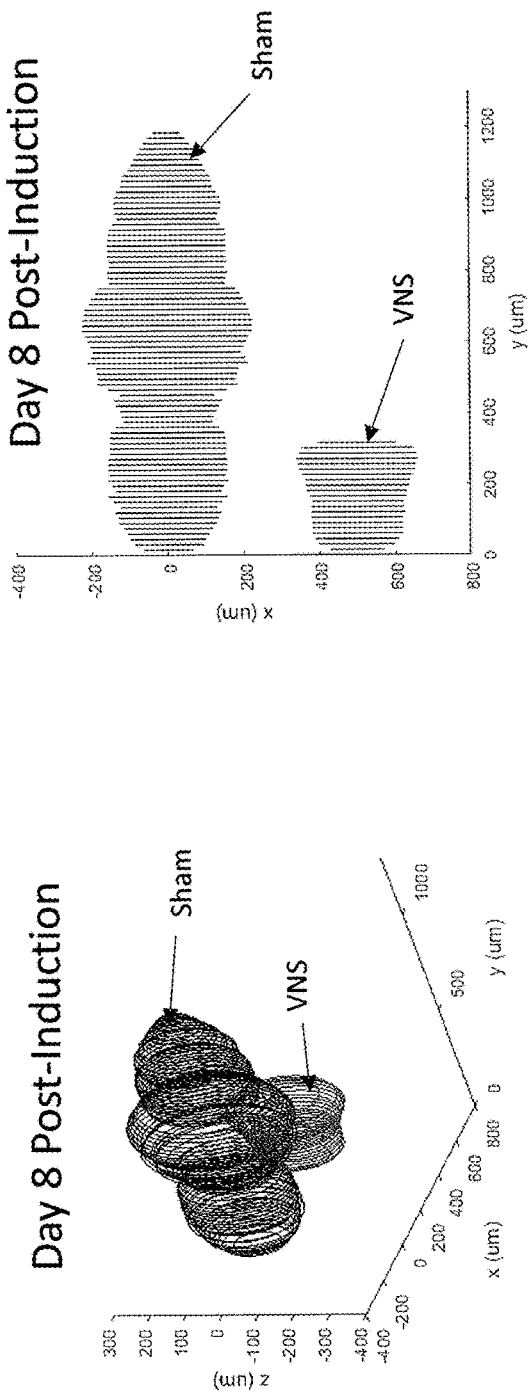
FIG. 5B
FIG. 5C

VAGUS NERVE STIMULATION TO TREAT NEURODEGENERATIVE DISORDERS

CROSS REFERENCE TO RELATED APPLICATIONS

This patent application claims priority to U.S. Provisional Patent Application No. 62/572,374, filed on Oct. 13, 2017 (titled "VAGUS NERVE STIMULATION TO TREAT NEURODEGENERATIVE DISORDERS") and U.S. Provisional Patent Application No. 62/576,547, filed Oct. 24, 2017 (titled "VAGUS NERVE STIMULATION TO TREAT NEURODEGENERATIVE DISORDERS") each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate generally to apparatuses (e.g., devices, systems) and methods for vagus nerve stimulation to treat neurodegenerative and neuroinflammatory disorders, and more specifically apparatuses and methods for vagus nerve stimulation to reduce demyelination and/or to promote remyelination to treat various neurodegenerative disorders such as multiple sclerosis.

BACKGROUND

A variety of central nervous system (CNS) demyelinating disorders, including multiple sclerosis, acute disseminated encephalomyelitis and neuromyelitis optica spectrum disorders, are difficult to effectively treat. For example, multiple sclerosis (MS) is a neurodegenerative disease characterized by demyelination of nerves in the central nervous system. Although the root cause of demyelination is not well understood, it generally is associated with the formation of lesions on the myelin sheaths and inflammation. Currently, there is no known cure for MS. Current treatments, with modest success, are primarily directed to treating acute attacks and reducing the frequency of attacks in the relapsing-remitting subtype of the disease or treating the symptoms. However, current therapies at best only slow the progression of the disease, and no therapy to date has demonstrated an ability to remyelinate nerves.

Therefore, it would be desirable to provide additional treatment methods and systems that can be used independently or in conjunction with other therapies to reduce the rate or amount of demyelination. Furthermore, it would desirable to provide a therapy that remyelinates nerves and reverses the progression demyelination. In addition, it would be desirable to reduce inflammation in the nervous system.

SUMMARY OF THE DISCLOSURE

The present invention relates generally to vagus nerve stimulation to treat neurodegenerative disorders, and more specifically to vagus nerve stimulation to reduce demyelination and/or promote remyelination to treat various neurodegenerative disorders such as multiple sclerosis.

For example, described herein are apparatuses (e.g., devices and/or systems) for reducing demyelination and/or increase remyelination by stimulation of a vagus nerve. These apparatuses may be implants or implanted into the patient's body. Any of these apparatuses may include: a biosensor configured to detect one or more biomarkers; a stimulator configured to apply stimulation to the vagus nerve; and a controller coupled to the biosensor and the stimulator and configured to apply stimulation to the vagus nerve from the stimulator sufficient to reduce demyelination and/or increase remyelination of nerves within the patient when the biosensor detects a biomarker indicative of demyelination. In some variations, these apparatuses include an implant comprising a stimulator (e.g., a waveform and/or pulse generator, an oscillator, a power supply and/or power regulation circuit, etc.), a stimulation applicator (e.g., one or more electrodes, mechanical transducers, etc.), and a controller. The controller may be configured as a microcontroller and may be in electrical communication with the stimulator so as to control operation of the stimulator. The controller may include one or more processors, a memory and/or a timer. The stimulator and/or controller may be in electrical communication, one or more stimulation applicators. In some variations the controller may include or be in communication with wireless communications circuitry for wirelessly communicating with one or more remote processors. The remote processor may be a hand-held device (e.g., smartphone, wearable electronics, etc.). The controller may optionally be in communication with one or more biosensors that may be included with the implant or may be remote from the implant (e.g., may be wearable, single-use, etc.). In some variations the biosensors are wirelessly connected to the apparatus.

In some variations the apparatus may be used without a biosensor. For example, the apparatus may be configured to periodically and/or on demand apply VNS treatment to prevent or reduce demyelination. The apparatus may be configured to apply VNS treatment doses once multiple times per day (e.g., 1× day, 2×, day, 3×, day, 4× day, 5× day, 6× day), or every other day, or every 3 days, etc. In some variations the apparatus may be configured to both automatically apply a VNS treatment dose on a predetermined and/or adjustable scheduled, as well as provide VNS treatment doses based on input from a user (e.g., patient, physician, etc., including "on demand" doses) and/or based on detection of a biomarker indicative of an actual or potential increase in demyelination.

In any of these variations, a biosensor may be configured to detect one or more markers (e.g., biomarkers) from the patient's body, including from the patient's blood and/or cerebrospinal fluid. Examples of biomarkers may be found herein. The biosensor may be part of the implanted apparatus, or it may be connected to the apparatus (e.g., the controller) via a wired or wireless communication. The biosensor may be configured to detect any biological marker, including chemical markers (e.g., a protein, nucleotide, e.g., RNA, DNA, microRNA, etc., lipid, carbohydrate, etc.), as well as functional markers (nerve conduction, etc.), body temperature, and the like. For example, in some variations, the biosensor is configured to detect temperature.

In general, the apparatuses described herein may be configured to be inserted or implanted into the body. For example, the apparatus may be configured to be implanted. The apparatus may include a stimulation applicator (also referred to as simply a stimulator or a VNS treatment stimulator) that may be a mechanical and/or electrical stimulator. A mechanical stimulator may be a piezoelectric driver that may vibrate and/or apply pressure to the tissue, including to the vagus nerve, in the VNS treatment parameters, such as mechanical stimulation of the vagus nerve at between 1-2 kHz for a treatment time (e.g., between 1 ms and 5 minutes, e.g., 10 ms-10 sec, etc.). Alternatively or additionally, the stimulation applicator may be an electrical stimulation applicator and may include one or more (e.g., two or more) electrodes configured to apply electrical stimulation to the vagus nerve. For example, electrical stimulation of about 0.1 mA to 10 mA (e.g., between 1 mA-5 mA), at a frequency of between about 1 Hz and about 2 kHz (e.g., between about 1-100 Hz), where the pulses applied have a pulse width of between about (50-500 usec, e.g., between about 100-300 usec). The controller may be configured to enforce an 'off-time' following a VNS treatment dose of between about 10 minute and 12 hours (e.g., between about 2 hours and 10 hours, between about 3 hours and 6 hours, at least 2 hours, at least 3 hours, at least 4 hours, at least 5 hours, at least 6 hours, etc.). For example, the stimulator may include an electrode configured to apply electrical energy to the vagus nerve.

In some variation the apparatus is configured to apply VNS treatment to the patient in which the VNS treatment is electrical stimulation. For example, the VNS treatment may include the application of electrical energy at between about 1-100 Hz (e.g., between about 1-50 Hz, between about 1-20 Hz, between about 5-30 Hz, between about 5-15 Hz, approximately 5 Hz, approximately 10 Hz, approximately 15 Hz, etc.). The energy may have a peak amplitude of between about 0.1 mA and about 2 mA (e.g., between about 0.2 mA and about 1.8 mA, between about 0.5 mA and about 1.5 mA, between about 0.5 mA and about 1 mA, between about 0.1 mA and about 1 mA, approximately 0.5 mA, approximately 0.75 mA, approximately 1 mA, etc.). Alternatively the applied energy may have an average amplitude of between about 0.1 mA and about 2 mA (e.g., between about 0.2 mA and about 1.8 mA, between about 0.5 mA and about 1.5 mA, between about 0.5 mA and about 1 mA, between about 0.1 mA and about 1 mA, approximately 0.5 mA, approximately 0.75 mA, approximately 1 mA, etc.). The applied energy is typically pulsed, and may be pulsed square waves, sinusoidal waves, triangular waves, etc. The applied energy may be biphasic or monophasic. For example, the applied energy maybe biphasic. The applied VNS treatment may be a constant biphasic pulse train having a frequency of between 1-100 Hz (e.g., 10 Hz) and a peak amplitude of between about 0.5 mA and 2 mA (e.g., approximately 0.75 mA). Any of the methods for treatment described herein may be configured to apply this type of VNS treatment.

Any of the apparatuses (e.g., devices, systems, etc.) described herein may be configured to be implanted on the vagus nerve. Thus, any of these apparatuses may be implanted via a nerve sheath or nerve cuff configured to secure the apparatus onto the nerve and/or prevent movement of the apparatus relative to the nerve and/or insulate the apparatus from other tissues. The implanted apparatus may be implanted in any appropriate location on the nerve, including one or around the vagus nerve at the upper chest, or on or around the vagus nerve at a sub-diaphragmatic location. The implant may be a leadless implant that is connected to the vagus (see, e.g., U.S. Pat. Nos. 8,412,338, 8,612,002, 8,886,339, and 8,788,034, each of which is herein incorporated by reference in its entirety). For example, any of these apparatuses may include a nerve cuff configured to secure the stimulator to the vagus nerve. Alternatively, any of these apparatuses may include a lead connecting the micro stimulator and/or other components to the stimulation applicator on/around the vagus nerve via one or more leads.

As mentioned, any of these apparatuses may be configured to apply VNS treatment comprising a low duty-cycle electrical stimulation of between about 0.25 mA and about 5 mA to the vagus nerve for less than about 2 minutes. The apparatus may be configured to provide an off-time of at least x minutes/hours (e.g., 10 minutes, 20 minutes, 30 minutes, 40 minutes, 60 minutes, 2 hours, 3 hours, 4 hours, etc.).

Any of the apparatuses described herein may be configured to perform a method of reducing demyelination in a patient diagnosed with or at risk of a disorder involving demyelinated nerves (e.g., including but not limited to methods of treating a disorder and/or disease associated with demyelination, such as multiple sclerosis). For example, a method of reducing demyelination (and/or a method of increasing remyelination) may be a method comprising detecting a marker for demyelination and applying stimulation to the vagus nerve to reduce demyelination of nerves within the patent.

Applying stimulation to the vagus nerve includes applying VNS treatment and may comprise, for example, applying electrical stimulation of between about 0.25 and about 5 mA to the vagus nerve for less than about 2 minutes. In some variations this may include waiting for an off-time (e.g., an off-time of at least 10 minutes, 30 minutes, 1 hour, 2 hours, 3 hours, 4 hours, etc.).

Any of these methods may include applying non-invasive stimulation to the vagus nerve. For example, the simulation may be through a transdermal (e.g., via a surface electrode and/or mechanical stimulation, including ultrasound) route over a portion of the vagus nerve. The vagus nerve includes a number of branches or extensions that may be accessed and/or targeted from outside of the body either mechanically and/or electrically. For example, non-invasive application may include ultrasound stimulation of the vagus nerve. Any of these methods may include applying transdermal electrical stimulation (TENS), or the like.

Any of the methods described herein may include monitoring, e.g., periodically, on demand, and/or continuously, one or more markers (e.g., biomarkers) for demyelination or a risk of demyelination. As mentioned, any appropriate method or apparatus for monitoring demyelination or a risk of demyelination may be used. For example any of these methods may include detecting a marker for demyelination comprising monitoring the patient's temperature. A change (including an increase) in core body temperature has been linked to an increase in symptoms in demyelination disorders, including but not limited to MS.

Any of the methods and apparatuses described herein may be used with or linked to markers for the integrity of the blood-brain barrier. The methods and apparatuses described herein generally improve the integrity of the blood-brain barrier. Thus, any marker linked to leakage or loss of integrity of the blood-brain barrier may be used to trigger VNS therapy as described herein. Examples of markers may include Serum S100β, as well as imaging modalities such as contrast-enhanced magnetic resonance imaging, CT-scan and lumbar puncture.

A detection of one or more markers (e.g., biomarkers) for demyelination may include determining a level of tumor necrosis factor in a blood or cerebrospinal fluid sample.

For example, described herein are methods (e.g., methods of treating a demyelination disorder, such as but not limited to MS, and/or methods of reducing or reversing demyelination) that include: detecting demyelination in a patient, and applying stimulation to the vagus nerve to increase the remyelination of nerves within the patent.

For example, any of these methods may include repeatedly applying a low duty-cycle electrical stimulation of between about 0.25 and about 5 mA to the patient's vagus nerve for less than about 2 minutes, followed by an off-time (e.g., of between about 10 minutes and about 48 hours) before the next stimulation.

Any of these methods and apparatuses may also include or be adapted to include the concurrent (immediately before, during or after, including systemically and/or locally) treatment with one or more pharmacological agents, particularly those that are believed to help with a demyelinating condition, such as (but not limited to) MS. For example, any of these method may include concurrently treating with a pharmacological agent such as one or more of: interferon beta-1a, interferon beta-1b, glatiramer acetate, glatiramer acetate, peginterferon beta-1a, daclizumab, teriflunomide, fingolimod, dimethyl fumarate, alemtuzumab, mitoxantrone, ocrelizumab, natalizumab.

As mentioned, any of the methods and apparatuses described herein may include continuously monitoring the patient for demyelination or a condition implicated in demyelination. For example, any of these methods and apparatuses described herein may include monitoring the patient for a marker related to a diseased selected from the group consisting of neurodegenerative diseases, neuroinflammatory diseases, and neuropathies. In some examples, the method includes detecting demyelination in a patient by detecting a marker related to MS. For example, the marker (e.g., biomarker) may be selected from the group including: neurofilament, glial fibrillary acidic protein, the monocyte macrophage marker CD163, the glial activation marker YKL-40, the B cell chemoattractant CXCL13, miRNA, mRNA, myelin reactive t cells, Kir4.1 antibodies, osteopontin, and microbiome associated lipopeptides.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1 illustrates a typical example of the 4 epochs that follow lysolecithin injection to the spinal cord in a model used to study multiple sclerosis.

FIGS. 2A and 2B illustrate the experimental protocols used to study demyelination and remyelination.

FIG. 4A is a graph showing the effect of vagal nerve stimulation (VNS) on demyelination with various levels of stimulation (0 mA, 0.25 mA, and 0.75 mA) four days following inducing of a demyelinating lesion. FIG. 4B shows the increase in remyelination by two weeks after inducing the demyelinating lesion without VNS treatment (0 mA) and with VNS treatment (0.75 mA), showing a rapid remyelination when VNS is applied. FIG. 4C is a 3D graph of the lesion size variation by depth at four days post induction of the demyelinating lesion with and without VNS treatment. FIG. 4D is a 2D projection graph of the median lesion four days post-induction of the demyelinating lesion comparing sham (no VNS treatment) and VNS treatment.

FIGS. 5A-5G are graphs that show that vagus nerve stimulation increased the rate and/or amount of remyelination. FIG. 5A is a graph showing the change in demyelination (determined by the change in induced lesion volume) following induction of demyelination with and without VNS treatment, showing an approximately 65% reduction in the area under the lesion volume ($mm^3$)/days post induction. FIG. 5B is a 3D representation of the demyelination (lesion) size variation with depth for no VNS treatment (sham) and VNS treatment. FIG. 5C is a 2D projection of median lesion volume eight days post-induction of demyelination (e.g., lesion) with VNS treatment and without VNS treatment (sham). FIG. 5D is a 3D representation of demyelination (lesion size) variation with depth at day 14 following inducing of demyelination (day 14 post induction) with VNS treatment (VNS) and without VNS treatment (sham). FIG. 5E is a 2D projection of median demyelination (lesion) at two weeks post-induction of demyelination with VNS treatment and without VNS treatment ("sham"). FIG. 5F is a 3D representation of demyelination (lesion size) variation with depth at day 21 following inducing of demyelination (day 14 post induction) with VNS treatment (VNS) and without VNS treatment (sham). FIG. 5G is a 2D projection of median demyelination (lesion) at three weeks post-induction of demyelination with VNS treatment and without VNS treatment ("sham").

In FIG. 9, CD3+T cell infiltration was significantly decreased in the VNS group on Day 3 post-LPC induction compared to Sham group by 50%.

FIG. 9 illustrates macrophage infiltration through a model of the blood-brain barrier is significantly decreased 24 hours post-demyelination induction (e.g., via LPC) with VNS treatment compared to sham (no VNS treatment) by 55%.

DETAILED DESCRIPTION

Figure 2B:
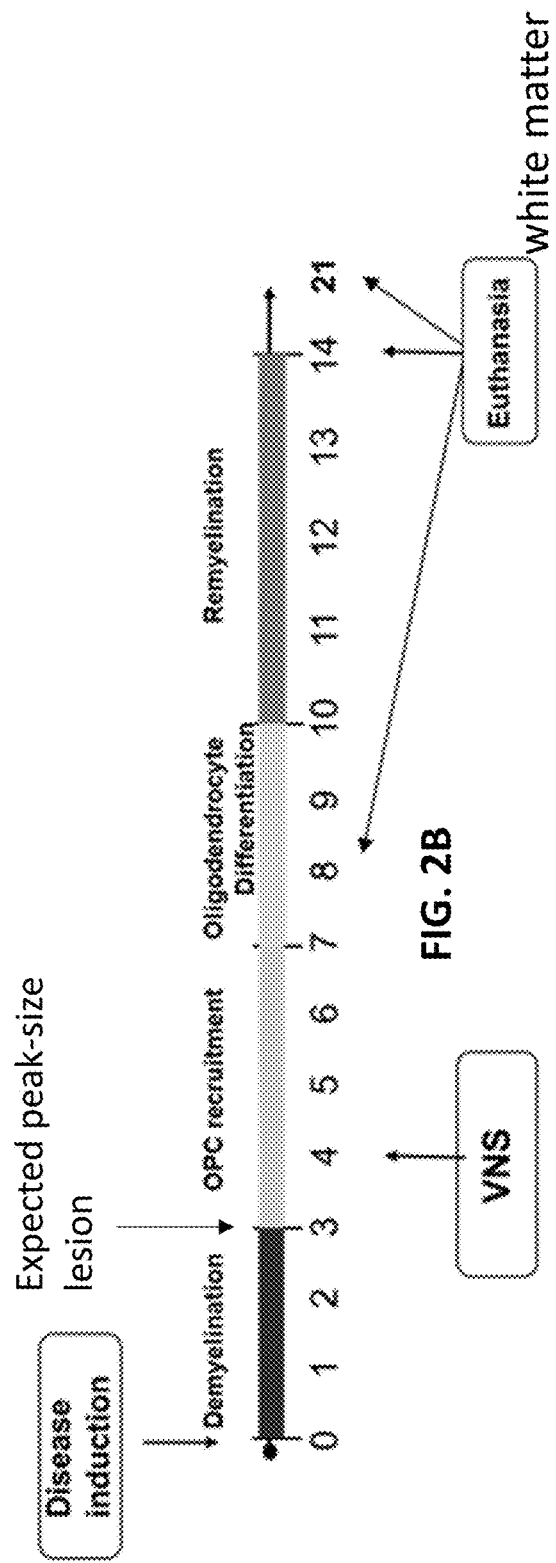

Electrical and/or mechanical stimulation of the cholinergic anti-inflammatory pathway (NCAP) by stimulation of the carotid vagus nerve been well described. For example, see U.S. Pat. Nos. 6,838,471, 8,914,114, 9,211,409, 6,610,713, 8,412,338, 8,996,116, 8,612,002, 9,162,064, 8,855,767, 8,886,339, 9,174,041, 8,788,034 and 9,211,410, each of which is herein incorporated by reference in its entirety. It has not previously been suggested that vagus nerve stimulation may be used to prevent or reduce demyelination and/or improve remyelination. Vagus nerve stimulation, through activation of both efferent and afferent pathways (or primarily through one of the efferent or afferent pathway), may be able to reduce the inflammation associated with inflammatory diseases and disorders, thereby reducing the severity of the symptoms and/or slowing, stopping, or reversing the progression of the disease. Applicants have surprisingly found that the apparatuses (e.g., systems, devices, etc.) and methods described herein may be used to stimulate the vagus nerve to reduce demyelination and/or to increase or promote remyelination. Furthermore, although the use of VNS treatment to modulate inflammation has been thought to involve afferent pathways, remyelination and demyelination may involve the efferent pathway or both the afferent and efferent pathways.

Diseases (e.g., diseases and disorder of myelination) which may benefit from VNS include, but are not limited to, multiple sclerosis (MS), Alzheimer's disease, Parkinson's disease, Huntington's disease, Amyotrophic lateral sclerosis (ALS), chronic inflammatory demyelinating polyneuropathy (CIDP), and Batten disease. Neuropathies that may benefit from VNS include peripheral neuropathies, cranial neuropathies, and autonomic neuropathies.

Vagus Nerve Stimulation Systems and Devices

In some variations the devices described herein are electrical stimulation devices that may be implanted, and may be activated to apply current for a proscribed duration, followed by a period without stimulation. As described in the examples that follow, the stimulation protocol may comprise a very limited period of stimulation (e.g., an on-time of less than 5 minutes, 2 minutes, 1 minute, etc.) followed by an off-time (during which stimulation is not applied, and may be prevented from being applied) of extensive duration (e.g., greater than 10 minutes, 20 minutes, 30 minutes, 40 minutes, 50 minutes, 1 hour, 1.5 hours, 2 hours, 4 hours, 12 hours, greater than 20 hours, greater than 24 hours, greater than 36 hours, greater than 48 hours, etc.). The applied energy may be electrical energy that is a fixed current having a frequency that is within the range of about 0.5 mA to 5 mA (e.g., approximately 2 mA), at a frequency of between about 1 Hz and about 1000 Hz (e.g., between 1 Hz and 100 Hz, between 1 Hz and 30 Hz, between 10 Hz and 200 Hz, etc.), where the pulses applied have a pulse width of approximately (50-500 usec, e.g., a 200 usec pulse). Thus, the duty-cycle of the applied current may be extremely low, where duty cycle may refer to the ratio of on-time/(on-time plus off-time). The stimulation is applied at an extremely low duty cycle, where duty cycle may refer to the percent of on-time to the total on-time and off-time for the ongoing treatment. For example, low duty cycle may be less than about 10, 5, 4, 3, 2, 1, or 0.5 percent of on-time to the total on time and off-time. The effect may be seen relatively quickly, and may persist over the entire off-time.

In particular, the methods and apparatuses described herein may be applied as needed, e.g., when the patient expresses or is likely to express an increased risk for demyelination and/or is experiencing (or has experienced) demyelination. Alternatively or additionally, the methods an apparatuses may be applied as needed when the patient expresses or is likely to express, and/or is experiencing (or has experienced) a leakage through the blood-brain barrier.

For example, we show herein that a low level, low duty cycle stimulation protocol (as described herein) reduces demyelination and/or increases remyelination, and prevents and/or reduces leakage through the blood-brain barrier. The effectiveness of low level, low duty cycle vagus nerve stimulation (VNS therapy) administered on even a single day results in a reduction in demyelination and an increase in remyelination seen over the course of two to three weeks. This type of stimulation contrasts with the use of a high duty cycle stimulation used by others to modulate vagus-nerve mediated functions (such as heart rate, etc.), or treat disorders such as epilepsy and depression. An important finding here is that demyelination can be reduced and even more surprisingly, remyelination can be increased. This effect is corroborated at these low duty cycle parameters by examining the histology of the spinal cord as described later below. Although low duty cycle vagus nerve stimulation is effective and highly efficient at reducing inflammation, in some embodiments, a higher duty cycle stimulation can be used, such as a duty cycle that is greater than about 1, 2, 3, 4, 5, 10, 20, 30, 40, or 50 percent of on-time to the total on-time and off-time.

MS patients may experience circadian pattern disruptions to symptoms that may be associated with or caused in part by the circadian patterns of IL-6 levels. Optionally, drugs, such as steroids, can be used along with VNS to suppress nighttime spiking of IL-6. Similarly, VNS can be modulated, by altering the timing of the stimulations for example, to suppress nighttime spiking of IL-6 more effectively. However, one advantage of VNS is the relatively long duration of the effect after a single stimulation, which may allow suppression of IL-6 levels during both night and day, which may render unnecessary the need for supplementary drug treatment or alternative timings. In some embodiments, VNS can be given in the evening before sleep, such as 15, 30, 45, 60, 90, 120, 150, or 180 minutes before sleep, and may also be given at night during sleep, to ensure nighttime suppression of IL-6 levels. In some embodiments, the amplitude of stimulation during sleep can be lowered (e.g., less than 2, 1.5, or 1 mA) to avoid waking the patient. In some embodiments, IL-6 levels can be measured and/or monitored, and VNS can be modulated based on the measured and/or monitored IL-6 levels. Other cytokines may also be measured and/or monitored, such as IL-1, TNF, IFN-gamma, IL-12, IL-18, and GM-CSF. These other cytokines may be used instead of or in addition to IL-6, either in combination or singly.

The methods, devices and systems herein may be applied specifically to treat any disorder for which a reduction of demyelination and/or an increase in remyelination would be beneficial. For example, described herein are electrodes (e.g., cuff electrodes, microstimulators) that may be placed around the vagus nerve and may communicate with one or more stimulators configured to apply appropriate stimulation of the vagus nerve to modulate demyelination and/or remyelination. The stimulator may be implanted. In some variations the stimulator is integral to the electrodes, and may be charged externally. The extremely low duty-cycle of the technique described herein may allow the device to be miniaturized to a greater degree than previously suspected for the treatment of chronic disorders via an implantable device.

In general, a device or system for modulating demyelination and/or remyelination may include a stimulator element (e.g., an electrode, actuator, etc.) and a controller for controlling the application of stimulation by the stimulator element. A stimulator element may be configured for electrical stimulation (e.g., an electrode such as a cuff electrode, needle electrode, paddle electrode, non-contact electrode, array or plurality of electrodes, etc.), mechanical stimulation (e.g., a mechanical actuator, such as a piezoelectric actuator or the like), ultrasonic actuator, thermal actuator, or the like. In some variations the systems and/or devices are implantable. In some variations the systems and/or device are non-invasive. In general, the controller may include control logic (hardware, software, firmware, or the like) to control the activation and/or intensity of the stimulator element. The controller may control the timing (e.g., on-time, off-time, stimulation duration, stimulation frequency, etc.). In variations in which the applied energy is electrical, the controller may control the applied waveform (amplitude, frequency, burst duration/inter-burst duration, etc.). Other components may also be include as part of any of these device or system, such as a power supply (e.g., battery, inductive, capacitor, etc.), transmit/receive elements (e.g., antenna, encoder/decoder, etc.), signal generator (e.g., for conditioning or forming the applied signal waveform), and the like. In some embodiments, a rechargeable battery that may be inductively charged allows the stimulator to deliver numerous electrical stimulations before needing to be recharged. In other embodiments, one or more capacitors that can also be inductively charged can be used to store a limited amount of energy that may be sufficient to deliver a single stimulation or a daily amount of stimulations. This dramatically reduces the size and cost of the stimulator, but requires that the user charge the stimulator daily or before each use.

In one example, an implantable device for modulating demyelination and/or remyelination (and/or reducing or preventing leaking of the blood-brain barrier) includes an electrode for electrically stimulating the vagus nerve. The electrode may be, for example, a cuff electrode. The electrode may be connected (directly or via a connector) to a controller and signal generator. The signal generator may be configured to provide an electrical signal to the electrode(s). For example, the electrical signal may be an electrical waveform having a frequency of between about 0.1 Hz and about 1 KHz (e.g., 10 Hz), where the pulses applied have a pulse width of approximately (50-500 usec, e.g., a 200 usec pulse). The signal generator may be battery (and/or inductively) powered, and the electrical signal may be amplitude and/or voltage controlled. For example in some variations the device or system may be configured to apply a current that is between about 0.05 mA to 25 mA (e.g., approximately 0.5 mA, 1 mA, 2 mA, 3 mA, etc.). The electrical signal may be sinusoidal, square, random, or the like, and may be charge balanced. In general, the controller (which may be embodied in a microcontroller such as a programmed ASIC), may regulate turning on and off the stimulation. For example, stimulation may be applied for an on-time of between about 0.1 sec and 10 minutes (e.g., between 1 sec and 5 minutes, between 1 sec and 2 minutes, approximately 1 minute, etc.); the stimulation may be configured to repeat automatically once every x hours or days, e.g., every other day (off time of approximately 48 hours), once a day (e.g., with an off-time of approximately 24 hours), twice a day (off-time of approximately 12 hours), three times a day (off time of approximately 8 hours), four times a day (off time of approximately 6 hours), or the like. In some variations the implant may be configured to receive control information from a communications device. The communications device may allow modification of the stimulation parameters (including off-time, on-time, waveform characteristics, etc.). The communications device may be worn, such as a collar around the neck, or handheld.

In use, an implant may be configured to be implanted so that the electrodes contact or approximate the vagus nerve or a portion of the vagus nerve. In one variation the implant includes a cuff that at least partially surrounds the vagus (e.g., near the carotid region). The controller and/or signal generator (including any power source) may be formed as part of the cuff or may be connected to by a connector (e.g., wire).

In some variations the device may be non-invasive. For example, the device may be worn outside the body and may trigger stimulation of the vagus nerve from a site external to the body (e.g., the ear, neck, torso, etc.). A non-invasive device may include a mechanical device (e.g., configured to apply vibratory energy). In some variations the device is configured to apply ultrasound that may specifically target the vagus nerve and apply energy to activate the vagus nerve. In some variations, transcutaneous magnetic stimulation of the vagus nerve may be used.

In any of the variations described herein, the devices, system and methods may be configured to prevent desensitization of the signal in a way that would reduce or inhibit the modulation of demyelination and/or remyelination. For example in some variations, "over stimulation" of the vagus nerve, e.g., simulation at intensities that are too great or applied for too long, or outside of the frequency ranges described herein, may result in desensitization of the effect, thus further modulation may be limited or inhibited. Therefore, in some embodiments, the amplitude of stimulation may be restricted from exceeding (i.e., be less than) about 3 mA, 4 mA, or 5 mA, and/or the duty cycle may be restricted from exceeding about 1, 2, 3, 4, 5, 6, 7, 8, 9, 10, 15, 20, or 25%. In some embodiments, the amplitude is also at least 0.25 mA, 0.5 mA, 0.75 mA, or 1.0 mA.

The examples illustrated above may provide insight into the devices, systems and methods of use for stimulation of the vagus nerve to modulate demyelination and/or remyelination. These methods and devices may be used to treat any indication for which modulation of demyelination and/or remyelination would be beneficial. Non-limiting examples of indications include neurodegenerative and neuroinflammatory diseases such as multiple sclerosis (MS), Alzheimer's disease, Parkinson's disease, Huntington's disease, Amyotrophic lateral sclerosis (ALS), and Batten disease. Other examples include peripheral neuropathies, cranial neuropathies, and autonomic neuropathies. In general, these devices may offer alternative and in some ways superior treatment as compared to pharmacological interventions aimed at modulating demyelination and/or remyelination, and therefore may be used for any indication for which such pharmacological treatments are suggested or indicated. In some embodiments, the VNS treatments described herein can be used in conjunction with pharmacological treatments, particularly when the pharmacological treatment has a different mechanism of action than the VNS, which may lead to synergistic results.

Thus, the methods of modulating demyelination and/or remyelination as described herein may be used in conjunction with one or more pharmacological interventions, and particularly interventions that treat diseases associated with demyelination, neurodegeneration or neuroinflammation. For example, it may be beneficial to treat a subject receiving stimulation of the vagus nerve to modulate demyelination and/or remyelination by also providing agent such as intravenous corticosteroids (e.g., methylprednisolone), oral corticosteroids, interferons beta-1a and beta-1b, monoclonal antibodies (e.g., natalizumab, alemtuzumab, daclizumab and ocrelizumab), and immunomodulators (e.g., glatiramer acetate, mitoxantrone, fingolimod, teriflunomide, and dimethyl fumarate).

Thus, described herein are devices (VNS devices) for the treatment of neurodegenerative and/or neuroinflammatory disorders. Such devices are generally configured to apply low duty-cycle stimulation to the vagus nerve of a subject, as described in any of the variations (or sub-combinations) of these variations. In some embodiments, the patient is first diagnosed or identified with a neurodegenerative or neuroinflammatory disorder, particular a disorder characterized by demyelination or need for remyelination, before being implanted and treated with the VNS device.

In use, any of the methods described herein may include a step of monitoring for demyelination or demyelination-associated disorders, which may be determined through detection of a biomarker from blood and/or cerebrospinal fluid, and/or through medical imaging techniques such as MRI or CT scans. For example, as assay for an inflammatory cytokine (e.g., tumor necrosis factor) may be used to detect acute inflammatory episodes. Monitoring may be continuous or discrete (e.g., at one or more times, or time intervals). In addition or alternatively, biomarkers associated with multiple sclerosis or other neurodegenerative or neuroinflammatory diseases or neuropathies can be used for monitoring, depending on the disease being treated. See Housley, W. J., D. Pitt and D. A. Hafler (2015). "Biomarkers in multiple sclerosis." *Clin Immunol* 161(1): 51-58; and Katsavos, S. and M. Anagnostouli (2013). "Biomarkers in Multiple Sclerosis: An Up-to-Date Overview." *Mult Scler Int* 2013: 340508. For example, biomarkers found in MS serum and cerebrospinal fluid include markers of neurodegeneration including neurofilament and GFAP, the monocyte macrophage marker CD163, the glial activation marker YKL-40, the B cell chemoattractant CXCL13, miRNA and mRNA, myelin reactive t cells, Kir4.1 antibodies, osteopontin, and microbiome associated lipopeptides. Any of these biomarkers can be monitored and/or measured alone or in combination, and can be used as feedback to modulate VNS. Other biomarkers for treating MS patients in particular are listed in Table 1.

TABLE 1

Biomarkers in Multiple Sclerosis (A) Diagnostic biomarkers (criteria i, iv, v, and vi)

(1) Genetic-immunogenetic

| | | |
|---|---|---|
| HLA-DRB1*1501 | +++ Risk for MS | See also B, E |
| DR3 and DR4 haplotypes | ++ Risk for MS | |
| HLA-DRB1*04 | ++ Risk for MS | |
| HLA-DRB1*0401 | + Risk for high familial autoimmunity in MS patients | See also F |
| HLA-DQ1*0102 | + Risk for MS, in coexistence with HLA-DRB1*1501 | |
| HLA-DPB1*0501 | + Risk for opticospinal MS | |
| HLA-DPB1*0301 | + Risk for opticospinal MS | |
| IL2RA and IL7RA polymorphisms | + Risk for MS | |
| EVI5, CD58, KIAA0350, and RPL5 polymorphisms | +/− Risk for MS | |

(2) Laboratorial

| | | |
|---|---|---|
| OCB IgG | +++ But with low specificity | See also E |
| KFLC | +++ But with low specificity | See also E |
| MRZ reaction | +++ Higher specificity than OCB IgG | See also E, F |
| Anti BRRF2, anti EBNA-1 | ++ | See also B, C |
| Anti MBP 48-70 and 85-170 | + | See also B, E |
| Anti MBP 43-68 and 146-170 | + Differential diagnosis with OND's | See also B, E |
| MBP/MOG conformational epitopes antibodies | + But low specificity | See also B, E, F |
| VEGF-A | + Lower CSF levels in all disease forms, but low specificity | See also D, E |
| Vitamin D | +++ Lower levels, higher risk for MS | See also C, F |
| TRECs | + Lower serum levels in all disease forms, but low specificity | See also B |
| CSF levels of lipocalin 2 | + Higher CSF levels in MS, but low specificity | See also F |

TABLE 1-continued

| Biomarkers in Multiple Sclerosis | | |
|---|---|---|
| AR | +++ Differential diagnosis of MS and NMO | See also C, E |
| NO and NO metabolites | + Higher CSF and serum levels in MS, but low specificity | See also C, E |
| NF-L | ++ Higher CSF levels in MS patients | See also C, F |
| NAA | +++ Differential diagnosis of RRMS and NMO | See also D, E |
| GFAP | +++ Differential diagnosis of MS and NMO | See also C, E |
|  | + Differential diagnosis of MS and NMO | See also C, E |
| Nogo-A | ++ For MS forms with prominent neurodegenerative element | See also D |
| (3) Imaging | | |
| Contrast-enhanced T1 lesions | +++ | See also C |
| Hyperintense T2-weighted lesions | +++ | See also C, D, E |
| Corpus callosum DTI abnormalities | ++ Early diagnostic biomarker | See also E |
| MRS findings (glutamate/choline) | +++ | See also C, D, E |
| PET | ++ But still experimental | |
| EPs | +++ | See also |
| Motor EPs | +++ Spinal cord syndrome at presentation | C, |
| VEMPs | +++ Brainstem dysfunction | D, E |
| SSR | ++ Autonomic dysfunction assessment in MS patients | See also E |
| (B) Biomarkers of phenotypical expression (criteria ii, iv, v, and vi) | | |
| (1) Genetic-immunogenetic | | |
| HLA-DRB1*1501 | +++ Early disease onset | See also A, E |
| HLA-DRB1*1501 | + Risk for cognitive decline | |
| HLA-DRB1*01 | ++ Protection against malignant disease form | |
| ApoE ε4 | ++ Greater risk for mental disorders | |
| (2) Laboratorial | | |
| OCB IgM against myelin lipids | +/− Aggressive disease course | See also E |
| EBV antibodies | + Early disease onset | See also A, C |
| Anti-MBP | +++ ADEM-like onset in childhood MS | See also A, E |
| Anti-MOG | +++ Childhood MS, ADEM, isolated optic neuritis, anti-AQP4 (−) NMO | See also A, E, F |
| rMOG index | +++ Progressive disease forms | |
| IL-6 serum levels | +++ Age at onset | See also C |
| TRECs | ++ Lower levels PPMS | See also A |
| Amyloid- (1-42) | ++ Lower levels, higher risk for mental disorders | |
| (3) Imaging | | |
| UCCA atrophy | +++ Progressive disease forms | See also E |
| NAGM DTI abnormalities | +++ Progressive disease forms | |
| (C) Biomarkers of demyelination-neuroinflammation-relapse (criteria i, ii, iii, iv, v, and vi) | | |
| (1) Genetic-immunogenetic | | |
| TOB1 | +++ Underexpression, higher Th1 and Th17 percentage | See also E |
| (2) Laboratorial | | |
| EBV antibodies | + Higher inflammatory activity | See also A, B |
| CXCL13 | ++ Mobilizes B-cells, T-helper cells | |
| CXCL12 | +/− Neuroprotection against inflammation in EAE/experimental | |
| IFN-/TNF-a | +++ Th1 immune response | |
| IL-1 levels imbalance | + Triggering factor for neuroinflammation | |

TABLE 1-continued

| Biomarkers in Multiple Sclerosis | | |
|---|---|---|
| IL-6 | +++ B-cell and T-cell immunity link, Th17 immune response triggering factor | See also B |
| | ++ Correlation with relapse frequency in female MS patients | |
| IL-10 -592 position polymorphisms | ++ Regulation of CNS autoimmunity | |
| IL-15 | ++ BBB disruption, enhanced CD8(+) T cytotoxicity | |
| IL-33 | + Increase in IFN-γ and IL-17 in mice EAE | |
| sICAM-1 | ++ Higher levels, higher inflammatory activity | See also F |
| | +++ Higher levels in NMO than MS-marker of BBB disruption | |
| sVCAM-1 | +++ Higher levels in NMO than MS-marker of BBB disruption | See also F |
| Laminin 411 | ++ TH-17 enhancement | |
| 4 Integrin | ++ Correlation with gadolinium-enhanced lesions during CIS | See also E, F |
| Osteopontin | ++ Serum and CSF elevation during relapse | |
| Fetuin-A | +++ Overexpression in active demyelinating lesions | See also F |
| Vitamin D | +++ High levels, anti-inflammatory role-lower radiological disease activity | See also A, F |
| CSF mature B-cells/plasma-blasts | ++ Bigger accumulation, higher inflammatory activity | |
| CXCR3 | ++ Helps T-cells to enter the brain | |
| CX(3)CR1 | ++ CD4(+)CD28(−) cytotoxic cells biomarker | |
| CSF CCR2(+)CCR5(+) T cells | +++ Increase during MS relapse-osteopontin enhancement | |
| CD56 Bright NK | ++ Remission phase | |
| AR | +++ Biomarker of BBB disruption | See also A, E |
| MMP-9 | ++ Higher CSF levels during relapse | |
| Ninjurin-1 | ++ Upregulation in active demyelinating lesions | |
| MBP and fragments | +++ Higher CSF levels during relapse | See also F |
| B-Crystalline | +++ Over-expression in active demyelinating lesions | |
| NO and metabolites | ++ | See also A, E |
| 7-Ketocholesterol | ++ | |
| Glutamate | +++ Higher levels in active demyelinating lesions | |
| Cystine/glutamate antiporter | + Over-expression in active demyelinating lesions | |
| NF-L | +++ Higher CSF levels, especially the 3rd week after relapse onset | See also A, F |
| GFAP | ++ Higher levels during relapse | See also A, E |
| S100B | +/− Higher CSF levels during MS/NMO relapse | See also A, E |
| N-CAM | + CSF elevation at remission onset | |
| BDNF | ++ Lower levels inhibit demyelination and axonal loss | See also D, E, F |
| (3) Imaging | | |
| Contrast-enhanced T1 lesions | +++ Active lesions | See also A |
| Hyperintense T2-weighted lesions | ++ Combination of different mechanisms | See also A, D, E |
| MTR decrease | + Demyelination and axonal loss combined | See also D |
| DTI abnormalities | ++ Combination of different mechanisms | See also D, E |
| MRS findings (especially changes in glutamate and choline) | +++ Active lesions | See also A, D, E |
| DTS | ++ Promising but still experimental | See also D |
| EP's delayed conduction | ++ Demyelination biomarker | See also A, D, E |

TABLE 1-continued

Biomarkers in Multiple Sclerosis (D) Biomarkers of axonal loss-neurodegeneration (criteria i, iv, v, and vi)

*(1) Laboratorial*

| | | |
|---|---|---|
| VEGF-A | ++ Lower levels, higher risk for neurodegeneration | See also A, E |
| 14-3-3 | +/− Axonal loss | |
| NAA | +++ Axonal loss | See also A, E |
| BDNF | ++ Lower levels inhibit demyelination and axonal loss | See also C, E, F |
| Nogo-A | +++ Higher CSF levels, failure in axonal repair | See also A |

*(2) Imaging*

| | | |
|---|---|---|
| RNFL thinning | +++ Axonal loss in the optic nerve | See also E, F |
| Hyperintense T2-weighted lesions | ++ Combination of different mechanisms | See also A, C, E |
| Black holes | +++ Axonal loss | See also E |
| MTR decrease | ++ Demyelination and axonal loss combined | See also C |
| DTI abnormalities | ++ Combination of different mechanisms | See also C, E |
| MRS findings (especially NAA) | ++ | See also A, C, E |
| DTS | +++ Promising but still not widely accessible | See also C |
| Visual and motor EPs | ++ | See also A, C, D |

(E) Prognostic biomarkers-biomarkers of disability progression (criteria ii, iv, v, vi, and viii)

*(1) Genetic-immunogenetic*

| | | |
|---|---|---|
| HLA-DRB1*1501 | +/− Early progression from RRMS to SPMS | See also A, B |
| HLA-DRB1*1501 | + Worst brain atrophy measures | |
| HLA-DQB1*0301 | + Worst brain atrophy measures | |
| HLA-DQB1*0602 | + Worst whole and gray matter atrophy measures | |
| TOB1 | +++ Early conversion from CIS to CDMS | See also C |

*(2) Laboratorial*

| | | |
|---|---|---|
| OCB IgG | +++ Conversion from CIS to CDMS | See also A |
| KFLC | +++ Conversion from CIS to CDMS | See also A |
| OCB IgM | +/− Bad prognostic biomarker | See also B |
| MRZ reaction | +++ Conversion from CIS to CDMS | See also A, F |
| Anti-MBP | +/− Conversion from CIS to CDMS | See also A, B |
| Anti-MOG | +/− Conversion from CIS to CDMS | See also A, B, F |
| AR | ++ Marker of clinical severity in NMO | See also A, C |
| VEGF-A | ++ Lower levels, progression from RRMS to SPMS | See also A, D |
| NO and NO metabolites | ++ Higher CSF levels, longer relapses/higher disability progression rates | See also A, C |
| NF-H | +++ Higher CSF levels, progressive forms/bad prognostic biomarker | |
| NF-H and tau | +++ Combined high CSF levels, conversion from CIS to CDMS | |
| Tubulin/actin | ++ Higher CSF levels, progressive forms/worst disability scores | |
| NAA | +++ Lower CSF levels, progressive forms/worst disability scores | See also A, D |
| GFAP | ++ Higher CSF levels, progressive MS forms/worst disability scores | See also A, C |
| S100B | +++ Disability progression in NMO<br>+ Disability progression in NMO | See also A, C |
| BDNF | ++ Lower CSF levels in SPMS patients | See also C, D, F |

TABLE 1-continued

| Biomarkers in Multiple Sclerosis | | |
|---|---|---|
| Unblocked α4 integrin | + Prognostic factor of risk for PML | See also C, F |
| (3) Imaging | | |
| RNFL thinning | + Correlation with brain atrophy measures and disease progression | See also D, F |
| Hyperintense T2-weighted lesions | +/− | See also A, C, D |
| Black holes | +/− | See also D |
| Whole brain atrophy measures | ++ Worsening rates at MS onset, prognostic biomarker of disability after 8 years | |
| Gray matter atrophy measures | +++ Higher worsening rates, progressive forms/early CIS conversion to RRMS | |
| UCCA atrophy | ++ Progressive forms, good correlation with EDSS, bad prognostic in RRMS | See also B |
| DTI abnormalities | +++ Early prognostic biomarker of relapse | See also C, D |
| Corpus callosum DTI abnormalities | +++ Bad prognostic biomarker | See also A |
| Spinal cord DTI abnormalities | +++ Good correlation with EDSS scores | |
| Early MRS abnormalities | ++ Bad prognostic biomarker | See also A, C, D |
| Combined EPs | +++ Good prognostic biomarker, especially for benign disease forms | See also A, C, D |
| SSR | ++ Correlation with higher EDSS scores | See also A |
| (F) Biomarkers of therapeutical response (criteria i, iv, v, vi, and vii) | | |
| (1) Genetic-immunogenetic | | |
| HLA-DRB1*0401, 0408, 1601 | +++ Higher risk for developing neutralizing antibodies against IFN-B | See also A |
| (2) Laboratorial | | |
| MRZ reaction | ++ B-cell immunity targeted therapy | See also A, E |
| Anti-MOG | ++ B-cell immunity targeted therapy | See also A, B, E |
| Fetuin-A | +++ Decreased CSF levels in Natalizumab responders | See also C |
| MBP | +++ Decrease in CSF levels in methylprednizolone responders | See also C |
| CSF lipocalin 2 | ++ Decreased CSF levels in Natalizumab responders | See also A |
| Unblocked α4 integrin | +++ Therapeutical response to Natalizumab | See also C, E |
| NF-L | +++ Normalized CSF levels in Natalizumab responders | See also A, C |
| BDNF | +++ CSF elevation in Glatiramer Acetate responders | See also C, D, E |
| TRAIL | ++ Serum levels good predictors of response in IFN-B | |
| MxA | ++ Serum levels good predictors of response in IFN-B | |
| sVCAM | ++ CSF alterations in IFN-B responders | See also C |
| Th17 immune profil | +/− Immune response exacerbation by IFN-B | |
| Vitamin D | +++ Increased levels in IFN-B responders | See also A, C |
| sICAM-1 | + Lower levels in Cladribine responders | See also C |
| sE-Selectin | + Lower levels in Cladribine responders | |
| (3) Imaging | | |
| RNFL | +++ Biomarker of therapeutical efficacy for several agents | See also D, E |

Classification of biomarkers.
+++ very strong correlation, ++ strong correlation, + modest correlation, and +/− controversial correlation.
Criteria used for classification., (i) Biological rationale; (ii) clinical rationale; (iii) predictability of disease initiation, reactivation or progression, or of disease differentiation; (iv) sensitivity and specificity; (v) reproducibility; (vi) practicality; (vii) correlation with therapeutical outcome; (viii) correlation with prognosis and disability.
Biomarkers of more than one category are indicated in the third column.

The information described herein for the first time shows that stimulation of the vagus nerve modulates demyelination and/or remyelination and/or leaking through the blood-brain barrier. The examples provided herein are not intended to be comprehensive, but merely illustrate and embody certain variations of the invention. It is within the abilities of one of ordinary skill in the art to understand and apply, without undue experimentation, the invention as described herein.

Example 1

To study the effect of VNS on neurodegeneration and neuroinflammation, a lysolecithin (LPC)-induced MS model can be used. Lysolecithin is a bioactive pro-inflammatory lipid that is a detergent-like membrane solubilizing agent. A 1% solution of LPC can induce local demyelinating lesions when injected into the white matter of the spinal cord. Four distinct epochs occur over 14 days post-injection: (1) demyelination; (2) oligodendrocyte progenitor cell (OPC) recruitment; (3) differentiation; and (4) remyelination. FIG. 1 illustrates a typical example of the 4 epochs, where demyelination occurs from about days 0-3, OPC recruitment occurs from about days 3-7, OPC differentiation occurs from about days 7-10, and remyelination occurs from about days 10-14.

To induce a self-limited demyelinating lesion, spinal cords of female BALB/c mice were injected between T3-T5 with 1% LPC (0.5 µL at 0.25 µL/min). The procedure to inject the mice with LPC was as follows. The mouse was anesthetized and stabilized into a stereotaxic frame. A midline incision was made between the scapulae. The underlying fat pads were bluntly separated and the spinous process of the T2 vertebra was identified and a laminectomy was performed. A syringe was advanced to 0.3 mm into the spinal cord and 0.5 uL of LPC was injected at a rate of 0.250 uL/min for 2 min. The muscle and adipose tissue were sutured and the skin was closed with surgical staples VNS was performed as previously described (Olofsson, Levine, et al. 2015. Bioelectronic Medicine: 37-42) on Day 0 or Day 4 post-induction with LPC. More specifically, to study the effect of VNS on demyelination, VNS (0.75-1 mA, 250 µS pulse, 10 Hz) or sham VNS (0 mA) was performed immediately following LPC administration, and the mice were euthanized on the day of expected peak lesion volume (day 4 post-induction; *J Neurocytol* 24(10): 775-81). The demyelination experimental protocol is summarized in FIG. 2A.

Spinal cord lesion volumes/areas were quantified by myelin loss as assessed from luxol blue-stained, 15 µm serial sections. FIG. 3A shows an illustration of a typical cross-section of the spinal cord, and FIG. 3B shows a luxol blue stained cross-section of the spinal cord with a LPC induced lesion in the anterior *funiculus* of the white matter 5 days post-LPC injection. To study the effect of VNS on remyelination, VNS or sham VNS treatments was performed 4 days post-induction, mice were euthanized on days 8, 14, or 21 post-induction, and nerves were processed as above. The remyelination experimental protocol is summarized in FIG. 2B. Mean lesion volumes between groups were compared by t-test.

Results: The demyelination protocol illustrated in FIG. 2A showed that VNS inhibited demyelinated lesion progression compared to sham. On day 4 post-induction, the mice were euthanized and the spinal cord around the LPC injection site was sectioned and stained with luxol blue. As shown in FIGS. 4A-4D, the mean lesion volume in the VNS group (0.75 mA) was significantly lower than in the sham group (VNS=0.03 mm3±0.006, n=5, vs. Sham=0.09 mm3±0.009, n=4, p=0.0023). VNS at 0.25 mA resulted in a mean lesion volume similar to sham VNS.

Figure 3B:
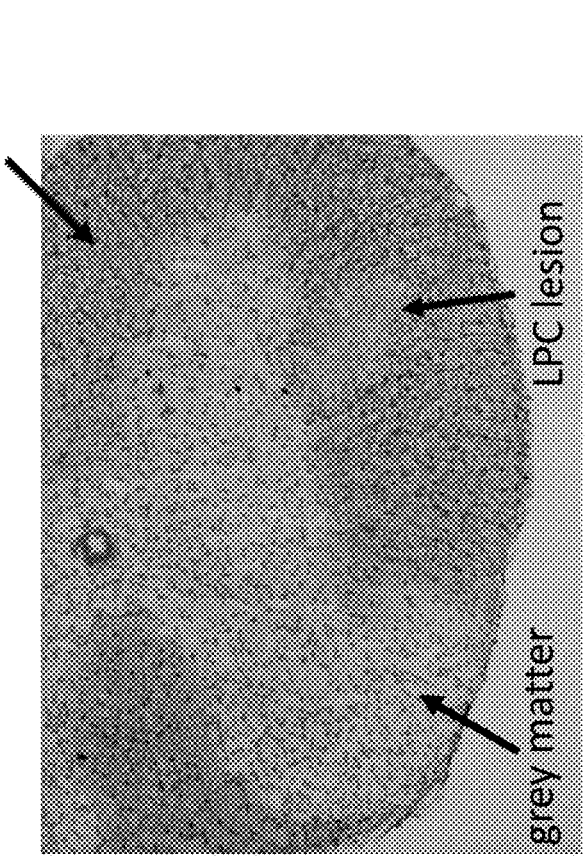
FIG. 3B illustrates a stained cross-section of a spinal cord with a lesion (which may be considered a demyelination) induced by lysolecithin injection.
Figure 3A:
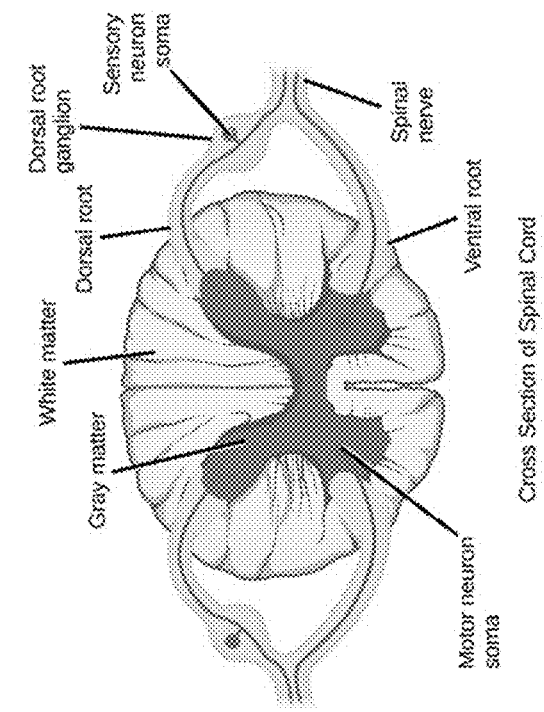
FIG. 3A illustrates a cross-section of a healthy spinal cord.
Figure 4B:
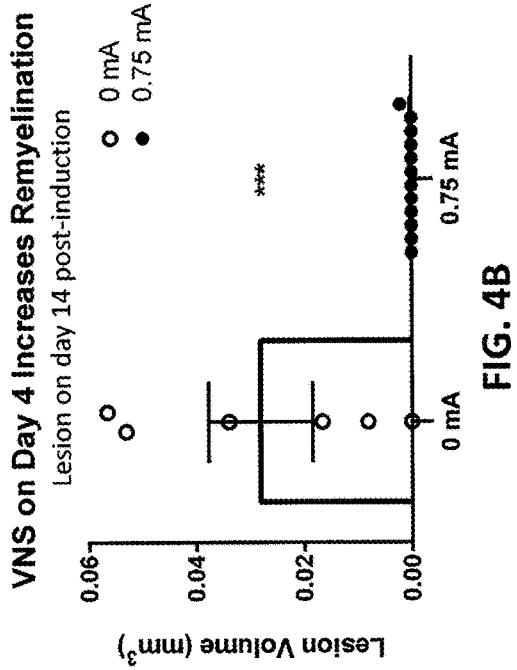
FIGS. 4A-4D are graphs that show that vagus nerve stimulation reduced the amount of demyelination that resulted from lysolecithin injection.
Figure 4D:
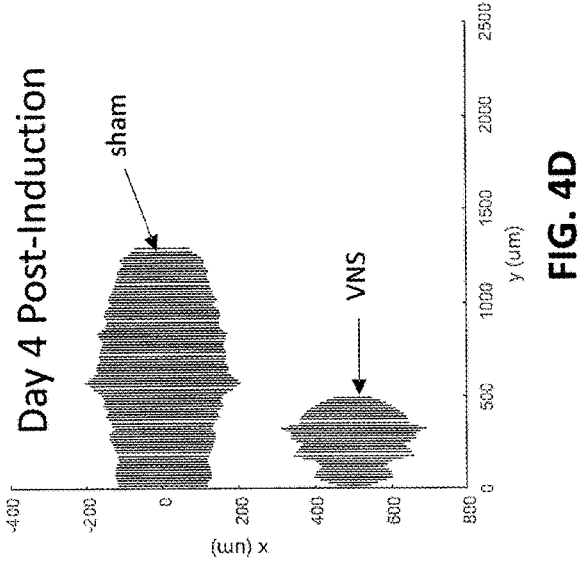
Figure 4A:
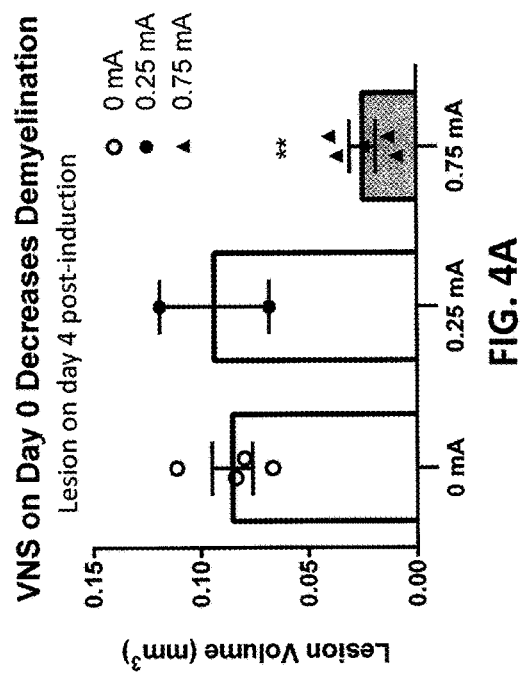
Figure 4C:
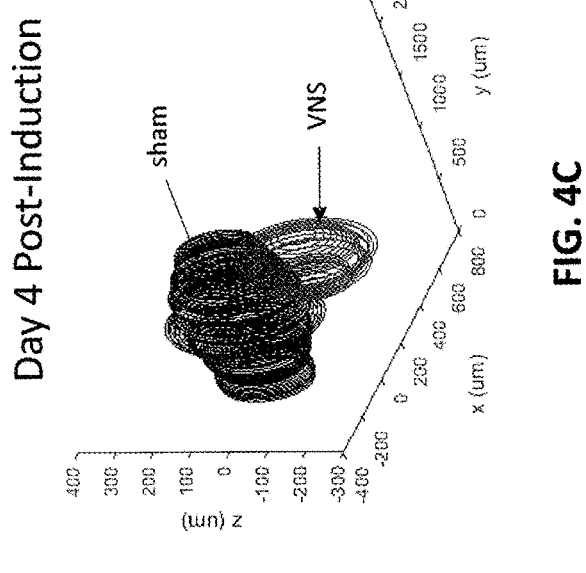
Figure 5D:
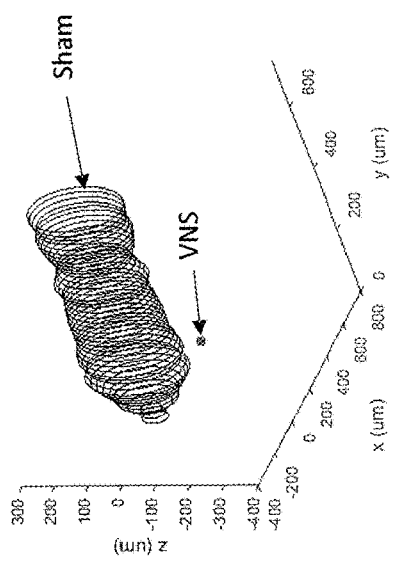
Figure 5E:
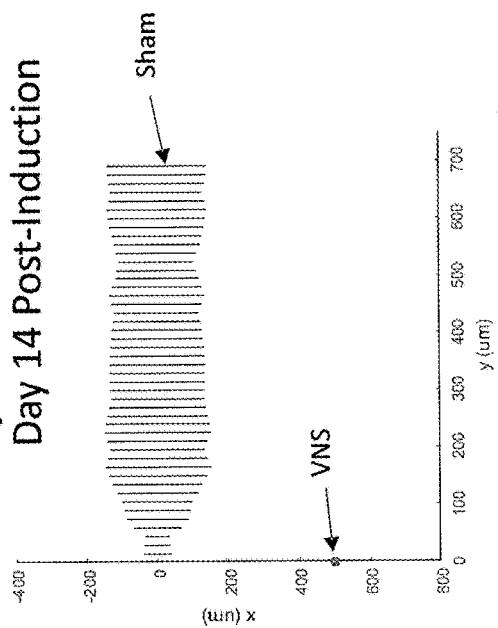
Figure 5F:
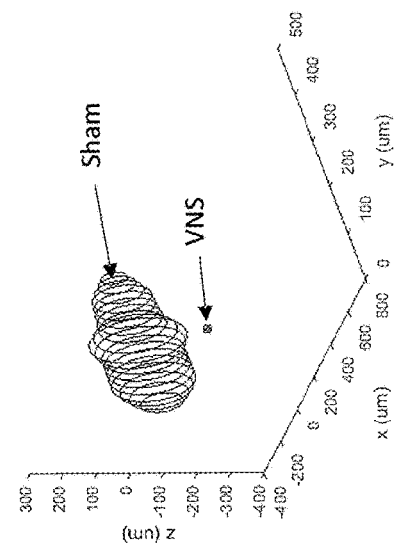
Figure 5G:
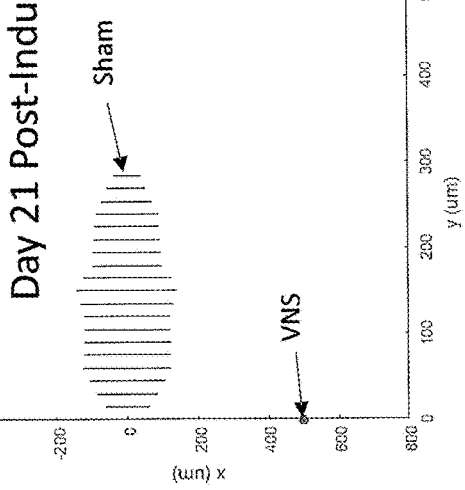

The remyelination protocol illustrated in FIG. 2B showed that remyelination occurred at a significantly accelerated rate in the VNS group. As shown in FIGS. 5A-5G, on day 8 post-induction, mean lesion volume in the VNS group was reduced to 0.02 mm3±0.01, n=4. On day 14 post-induction, mean lesion volume in the VNS group was significantly lower than in the sham group (VNS=0.0002 mm3±0.007, n=12, vs. Sham=0.03 mm3±0.01, n=6, p=0.0007). On day 14, 11 out of 12 VNS animals had no detectable lesion. By Day 21, the mean lesion volume in the sham group was 0.01 mm3±0.006, n=3. FIG. 5A shows that the area under the curve (AUC) between days 4 and 21 is reduced by about 65 percent with vagus nerve stimulation.

Conclusions: VNS reduced demyelination and accelerated remyelination, demonstrating a robust effect after a single dose in this model. Repeated stimulation of the vagus nerve with an implanted nerve stimulator may further reduce the rate of demyelination and/or further accelerate remyelination. This will be tested in an experimental autoimmune encephalomyelitis model to further assess the potential of VNS to treat MS.

Example 2

Figure 6B:
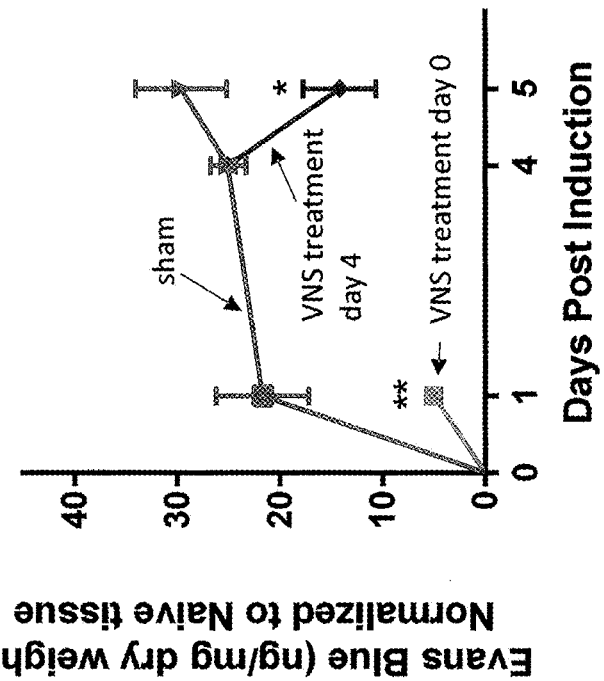
FIG. 6B illustrates the use of VNS treatment as described herein to reduce the leakiness of the blood-brain barrier following induced demyelination. VNS treatment before induced demyelination prevented the passage of dye (Evans blue) through the rat model of the blood brain barrier. VNS treatment after induced demyelination reduced and reversed the leakiness. VNS treatment on Day 0 (following LPC induction) significantly decreased leukocyte infiltration 24 hours post-stimulation, while VNS treatment on Day 4 post-LPC induction significantly decreases leukocyte infiltration 24 hours post-stimulation.
Figure 6A:
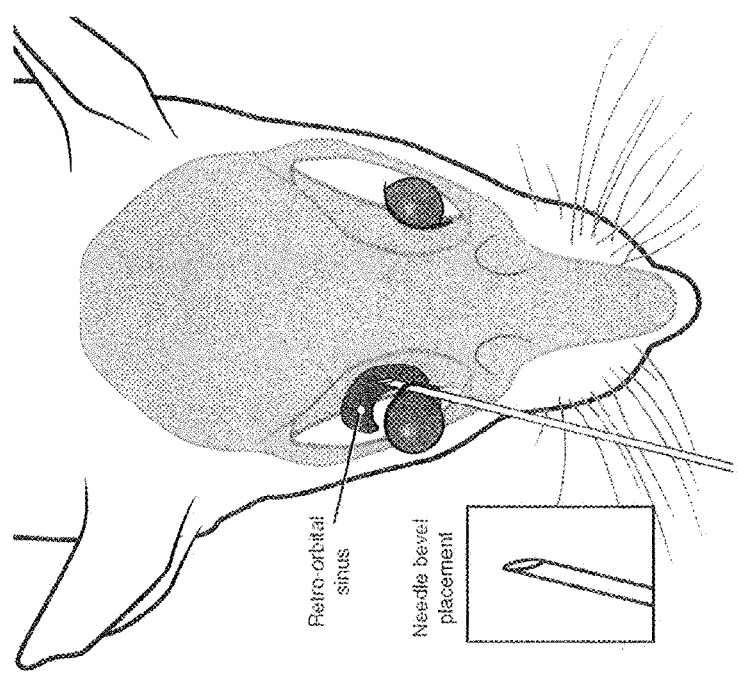
FIG. 6A shows the experimental protocol used to show the effect of VNS treatment as described herein on vessel leakiness following post-induction of demyelination.

Another study was performed to determine the effect of VNS on vessel leakiness 24 hours post-induction and stimulation. A lesion was induced as described above using LPC injection and VNS was performed immediately following induction. At 24 h, 0.15 mL of 1% Evans blue dye was injected intravenously through retro-orbital injection under anesthesia for 1 hr., as shown in FIG. 6A. One hour later, the animals were euthanized via cervical dislocation. Measurement of extravasation in the spinal cord (SC) was determined by extracting the SC and weighing the SC wet. The SC was then dried for 24 h at 56° C. and weighed dry. The Evans blue dye was extracted with a formamide solvent for 48 h at 56° C. incubation. The supernatant was measured spectroscopically at 620 nm and the quantity of Evans blue dye was determined by interpolation from a reference curve. The quantity of Evans blue dye was normalized to the dry weight of the SC. As shown in FIG. 6B, less Evans blue dye was extracted from the spinal cord from the mice that received VNS, which provides evidence that VNS reduces vessel leakiness 24 hours post-induction and stimulation. In addition, the amount of Evans blue dye extracted from the mice that received VNS was similar to the amount of Evans blue dye extracted from naïve mice (no LPC induced lesion).

Leakiness in the blood brain barrier may allow immune cells and inflammatory cytokines and chemokines to pass through and contribute to continued inflammation in the brain and/or spinal cord. Therefore, VNS may reduce vessel leakiness around the central nervous system (CNS), thereby reducing the recruitment of proinflammatory cells such as lymphocytes (e.g., T-cells) and macrophages to the brain and spinal cord, thereby reducing the inflammation in the CNS and reducing the amount demyelination that results from an inflammatory attack by the immune system.

Example 3

In general, the apparatuses and methods described for VNS therapy may also be used to prevent or treat increased leakiness of the blood-brain barrier, as illustrate in FIG. 6B.

Methods: 1% LPC was injected into the spinal cord white matter of BALB/c mice. For the first intervention time point, VNS therapy or sham VNS was performed immediately after injection. 24 hours later, mice (VNS, sham VNS, and naïve (no-LPC)) are injected with 1% Evans blue dye which binds to the albumin in blood and is left to circulate for 1 hour. Spinal cords are then harvested, dried for 24 hours in pre-weighed tubes at 60° C. Dried tissues are then incubated in formamide for 48 hours. Supernatant is then extracted from the tubes and read spectroscopically at 620 nm. For the second intervention time point, VNS therapy or sham VNS therapy occurs on day 4 post-LPC induction. On day 5 post-LPC induction, Evans blue extravasation is performed the same way as described for demyelination experiment. Evans blue concentration is compared (ng/mg of tissue) and normalized to naïve animals.

Results: LPC increased blood-spinal cord leakiness. VNS therapy significantly reduced Evans blue extravasation into the spinal cord compared to sham (81% decrease) 24 hours post-LPC induction (FIG. 6B). In addition, VNS therapy on day 4 post-LPC significantly reduced Evans blue extravasation on day 5 compared to sham (52% decrease).

Conclusion: VNS therapy increases the integrity of the blood-spinal cord barrier and subsequently reduces the extravasation of protein/Evans blue and other circulating species, including antibodies, DAMPS/PAMPS, and immunocytes into the central nervous system.

Example 4

Another experiment was performed to determine whether the effect of VNS on demyelination was α7 nicotinic acetylcholine receptor (nAChR) dependent. Two mice strains were used in the study. One mice strain is the C57 Black subtype 6 (C57BL/6), which is a common wild type strain that expresses α7 receptors and are denoted as α7+/+. The second mice strain is an α7 knockout strain of the C57BL/6 strain, which lacks the α7 receptor and are denoted as α7−/−. Each of the mice strains were given LPC injections in sham (no VNS) and VNS groups. Tissue extraction was performed 4 days post-injection. The procedure was essentially identical to the Balb/c mice demyelination experiments described above in Example 1.

Figure 7A:
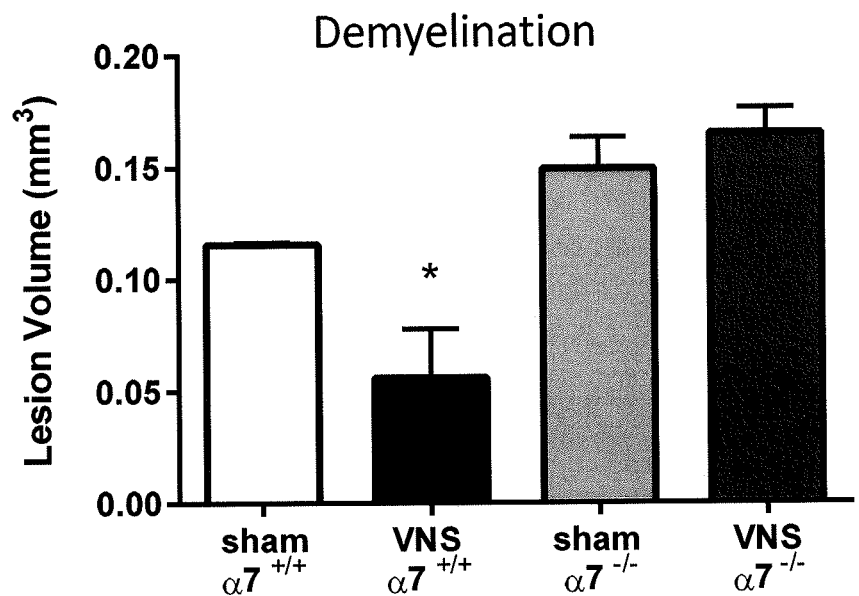
FIG. 7A illustrates the effect of the alpha-7 nicotinic acetylcholine receptors (a7 nAChR) in preventing demyelination re-myelination from VNS treatment (compared to sham without VNS treatment).
Figure 7B:
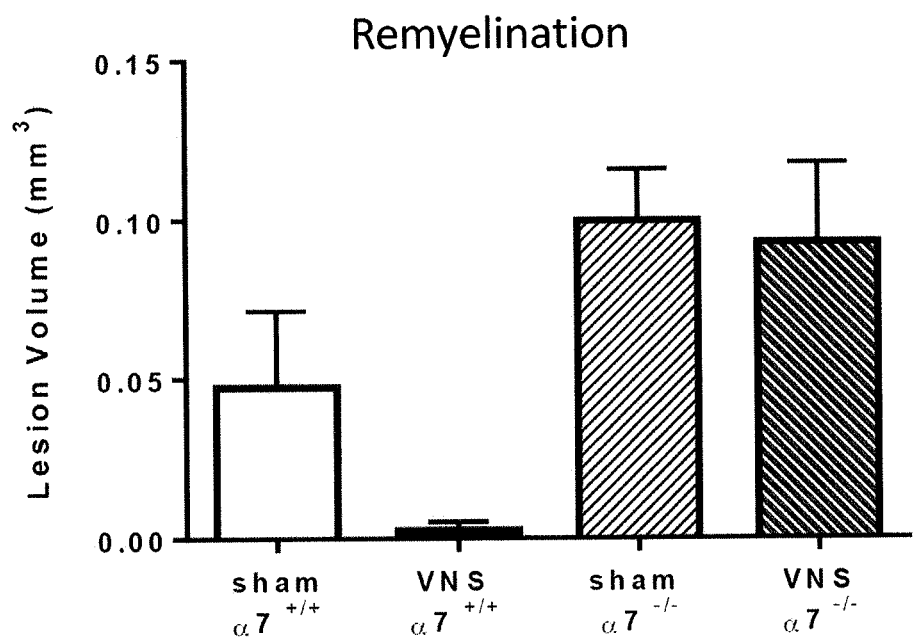
FIG. 7B illustrates the effect of the alpha-7 nicotinic acetylcholine receptors in increasing re-myelination from VNS treatment (compared to sham without VNS treatment).

As shown in FIG. 7A, the protective effects of VNS on demyelination is α7 nAChR-dependent. VNS treatment on mice with the α7 nAChR showed a reduced lesion volume when compared with sham, while VNS treatment on mice without the α7 nAChR showed no reduction in lesion volume when compared with sham. Similarly, the remyelination effect of VNS treatment may be α7 nAChR dependent, as shown in FIG. 7B. In this example, the effect of VNS treatment on remyelination in the presence (+/+) and absence (−/−) of the α7 nAChR due to either sham (no VNS treatment) or VNS treatment were examined, showing a substantial decrease in lesion volume, the maker for re-myelination following induction of a demyelination event (e.g., application of LPC.

In FIGS. 7A-7B, 1% LPC was injected into the spinal cord white matter of α7 nAChR knockout mice and C57BL/6 (wildtype) mice. For demyelination experiment, VNS treatment or sham VNS treatment, tissue collection, processing, and analysis are all the same as mentioned above for FIG. 1A. For remyelination, VNS and sham VNS intervention occurs the same as experiment described for FIG. 4B. Spinal cords are harvested only on day 8 post-LPC induction. Processing and analysis performed are the same as described for FIGS. 4A-4B.

Result: VNS therapy decreased demyelination in wildtype C57BL/6 mice. VNS therapy did not decrease demyelination in α7 KO animals (FIG. 7A). VNS therapy increased remyelination in wildtype animals, but did not increase remyelination in the knockouts (FIG. 7B). Thus, the effects of VNS on demyelination and remyelination are α7-dependent.

Example 5

Figure 8:
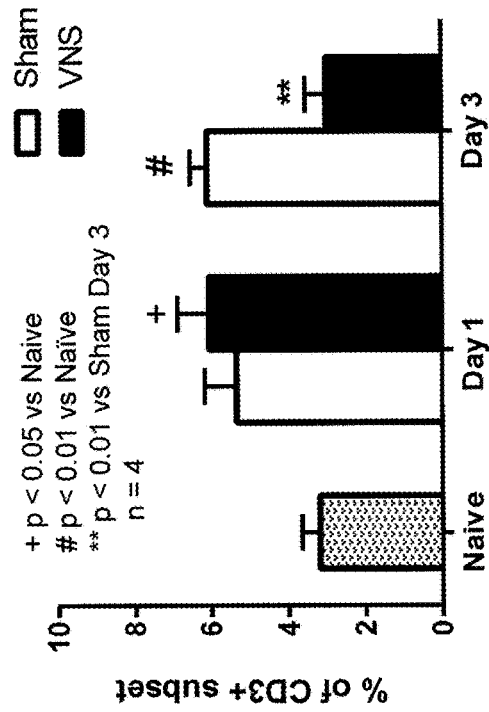
Figure 9:
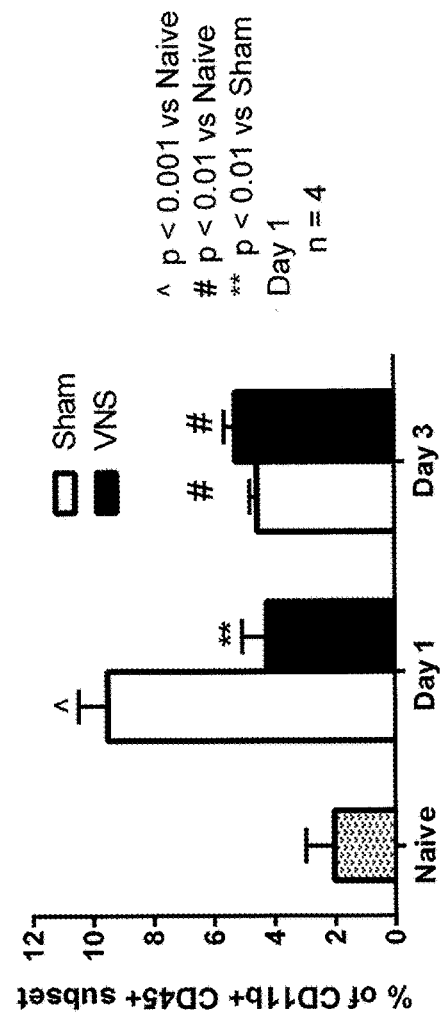
FIG. 9 shows the effect of VNS treatment as described herein to prevent or reverse leakiness of the blood-brain barrier compared to sham (no VNS treatment).

In general, the apparatuses and methods described for VNS therapy may also be used to prevent or treat increased immunocyte homing to the central nervous system, as illustrate in FIGS. 8 and 9.

In FIGS. 8 and 9, CD3+ T cell infiltration through a model for the blood-brain barrier is significantly decreased in the VNS treatment group. As shown in FIG. 8, the CD3+ T cell infiltration through the model of the blood-brain barrier on Day 3 post-LPC induction compared to Sham group is reduced by 50%. In. FIG. 9, the macrophage infiltration is significantly decreased 24 hours post-LPC induction in the VNS treatment group compared to the Sham (no VNS treatment) group by 55%.

Methods: Surgical procedures and VNS/sham VNS treatments remain the same from FIG. 4A. Spinal cords from VNS therapy, sham, and naïve mice are harvested on days 1 or 3 post-LPC induction. Tissue is then digested in enzymatic cocktail for 20 minutes at 37° C. followed by trituration and filtering through a 100 μM mesh screen. Single cell suspension is then put through a density gradient to remove myelin debris from glia cells and immune cells. Once isolated, cells are blocked in FACS buffer and CD32/CD19 for a half hour to prevent unspecific antibody staining. Cells are counted and checked for viability via hemocytometer. Cells are then placed in tubes, stained for either T cells (CD3+) or macrophages (CD11b+, CD45hi) and then analyzed via flow cytometer. Populations of cells are quantified using FlowJo program.

Result: LPC increased CD3+ T cell and macrophage infiltration in the spinal cord compared to naïve tissue (FIGS. 8 and 9). There was a significant reduction in CD3+ T cell infiltration on day 3 post-LPC induction in VNS therapy treated animals compared to sham (50% reduction) (FIG. 9). In addition, VNS therapy resulted in a significant decrease in macrophage infiltration compared to sham 1 day post-LPC induction (55% reduction) (FIG. 9). Thus VNS significantly reduces the infiltration of peripheral immunocytes into the CNS in this lysolecithin-induced MS model.

Figure 10A:
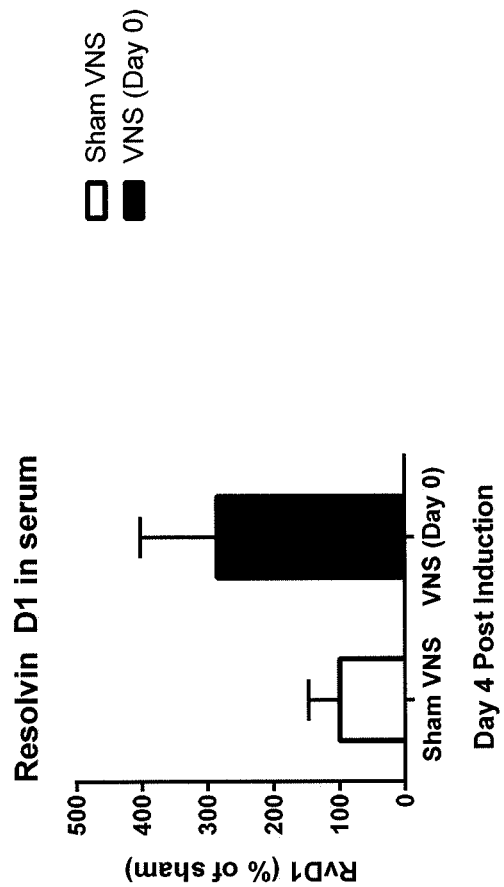
FIGS. 10A and 10B illustrate the effect of pro-resolution lipid Resolvin D1 following induction of demyelination with VNS treatment (VNS) and without VNS treatment (sham), showing Resolvin D1 (RvD1) is increased in VNS animals 4 days post-LPC induction compared to Sham animals and remains elevated 14 days post-LPC induction. Levels were decreased below that of the Sham 21 days post-LPC induction, by which time, no visible lesion is detected in VNS animals.
Figure 10B:
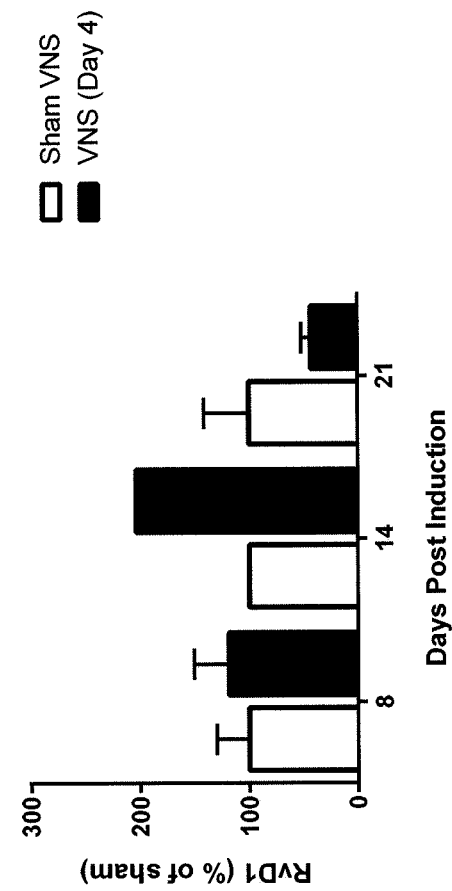

As shown in FIGS. 10A-10B, VNS therapy also increased re-myelination following a decrease in myelination. During spinal cord extractions for all prior experiments performed (see examples 1-4, above), blood was collected via cardiac puncture as well. Blood was centrifuged at 8,000×g for 5 minutes, the serum was collected and stored at −80° C. Using a Resolvin D1 ELISA kit, levels of RvD1 were measured spectroscopically from the serum of VNS and sham VNS mice for the demyelination (D4 harvest) and remyelination (D8, D14, and D21 harvests) experiments. Levels of RvD1 are analyzed (pg/mL) and represented as a percent of sham by day.

Result: as showing FIG. 10A, VNS therapy on day 0 (LPC-induction) increased serum levels of RvD1 on day 4. As shown in FIG. 10B, VNS on day 4 post-LPC induction also increased RvD1 in the serum levels of RvD1 with the highest concentration occurring on day 14 post-LPC induction. RvD1 levels in VNS serum were decreased as compared to sham at 21 days post-LPC induction, likely due to earlier resolution in the VNS group.

Thus, VNS therapy increases the pro-resolving lipid mediator RvD1 in serum which may contribute to the increased speed in resolution time of LPC-induced lesions compared to sham.

Example: System

Figure 11:
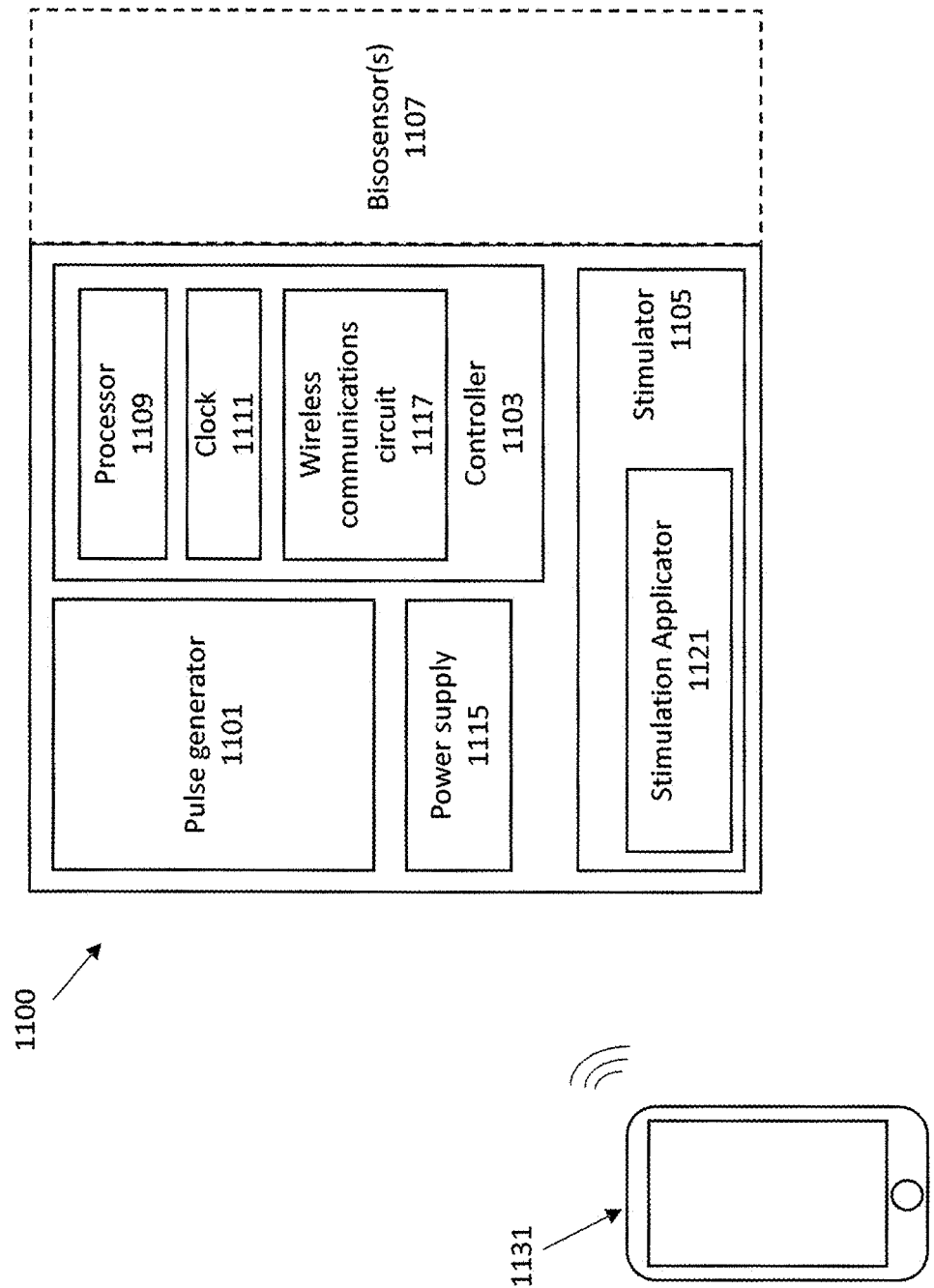
FIG. 11 schematically illustrates one example of an apparatus for reducing demyelination (e.g., increasing remyelination and/or reducing leakage through the blood-brain barrier), as described herein.

FIG. 11 schematically illustrates one example of a system 1100 for treating demyelination (e.g., for treating MS, or any other demyelinating disorders). In some variations the system for reducing demyelination and/or increase remyelination by stimulation of a vagus nerve includes a controller 1103, a stimulator 1105, and a pulse generator 1101. The pulse generator and stimulator may be connected to and controlled by the controller. In some variations all or some of the system may be implanted into the patient's body. All or some of the components of the apparatus may be enclosed by a housing (e.g., an implant housing). In general, the systems may also include one or more biosensor 1107 configured to detect one or more biomarkers. The biosensor may be coupled with the rest of the system (e.g., implant) or it may be separate and may communicate via a wired or wireless connection. For example the biosensor may be implanted into the body so as to sample blood, spinal fluid, or the like; in some variations the biosensor is external to the body and may be single use or configured for limited-reuse. In some variations the biosensor may include a sensor for determining a patient's physical condition (e.g., temperature, nerve conduction, etc.). In some variations the biosensor may be an immunochemical sensor configured to detect binding of one or more analytes and/or to provide a concentration.

The stimulator may be configured to apply stimulation to the vagus nerve. A stimulator maybe configured for electrical stimulation, mechanical stimulation, or both. For example, the stimulator may include or be coupled with the pulse generator 1101 (e.g., waveform and/or pulse generator, oscillator, etc.). The stimulator may include one or more stimulation applicators 1121 (e.g., one or more electrodes, mechanical transducers, etc.) for contact with the tissue, including the vagus nerve.

Any of the apparatuses may also include one or more power supplies 1115, and/or power regulation circuit, etc.

The controller is typically functionally coupled to the one or more biosensor (e.g., receiving data from the biosensor(s)) and controls the stimulator and may be configured to apply stimulation to the vagus nerve from the stimulator sufficient to reduce demyelination and/or increase remyelination of nerves within the patient when the biosensor detects a biomarker indicative of demyelination (including detecting active demyelination or a marker that is indicative of imminent active demyelination).

For example, a system may include an implant comprising a stimulator (e.g., a waveform and/or pulse generator, an oscillator, a power supply and/or power regulation circuit, etc.), a stimulation applicator (e.g., one or more electrodes, mechanical transducers, etc.), and a controller. The controller may be configured as a microcontroller and may be in electrical communication with the stimulator so as to control operation of the stimulator. The controller may include one or more processors, a memory and/or a timer. The stimulator and/or controller may be in electrical communication, one or more stimulation applicators. In some variations the controller may include or be in communication with wireless communications circuitry 1117 for wirelessly communicating with one or more remote processors 1131. The remote processor may be a hand-held device (e.g., smartphone, wearable electronics, etc.). The controller may optionally be in communication with one or more biosensors that may be included with the implant or may be remote from the implant (e.g., may be wearable, single-use, etc.). In some variations the biosensors are wirelessly connected to the apparatus.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An implantable system for reducing demyelination and/or increasing remyelination by stimulation of a vagus nerve, the implantable system comprising:
   a biosensor configured to detect one or more biomarkers for demyelination;
   a stimulator configured to apply stimulation to the vagus nerve; and
   a controller coupled to the stimulator and configured to receive input from the biosensor, the controller comprising control logic to control the activation of the stimulator to the vagus nerve from the stimulator sufficient to reduce demyelination and/or increase remyelination of nerves within a patient when the control logic determines that the biosensor detects a biomarker for demyelination at a level that exceeds or falls below a predetermined threshold indicative of demyelination.

2. The system of claim 1, wherein the biosensor is configured to detect a biomarker from the patient's blood and/or cerebrospinal fluid.

3. The system of claim 1, wherein the controller is configured to apply a low duty-cycle electrical stimulation of between 0.25 mA and 5 mA to the vagus nerve.

4. The system of claim 1, wherein the controller is configured to apply a low duty-cycle electrical stimulation, followed by an off-time of at least 10 minutes.

5. The system of claim 1, wherein the controller is configured to apply a low duty-cycle electrical stimulation for less than 2 minutes.

6. The system of claim 1, wherein the controller is configured to apply a low duty-cycle electrical stimulation of between 0.25 mA and 5 mA to the vagus nerve for less than 2 minutes, followed by an off-time of at least 10 minutes.

7. The system of claim 1, wherein the stimulator comprises an electrode configured to apply electrical energy to the vagus nerve.

8. The system of claim 1, further comprising a nerve cuff configured to secure the stimulator to the vagus nerve.

9. The system of claim 1, wherein the controller is configured to apply the stimulation for between 1 microsecond and 5 minutes followed by an off time of between 10 minutes to 12 hours.

10. A method of reducing demyelination and/or increasing remyelination in a patient diagnosed with or at risk of a disorder involving demyelinated nerves using an implantable system including a biosensor, a stimulator and a controller, wherein the method comprises:
    receiving data from the biosensor indicative of detecting a biomarker for demyelination; determining a level of the biomarker for demyelination; and applying stimulation to a vagus nerve from the stimulator when the biosensor detects the level of the biomarker for demyelination that exceeds or falls below a predetermined threshold that indicates demyelination, to reduce demyelination and/or increase remyelination of nerves within the patient.

11. The method of claim 10, wherein applying comprises applying a low duty-cycle electrical stimulation of between 0.25 mA and 5 mA to the vagus nerve.

12. The method of claim 10, wherein applying comprises applying a low duty-cycle electrical stimulation, followed by an off-time of at least 10 minutes.

13. The method of claim 10, wherein applying comprises applying a low duty-cycle electrical stimulation for less than 2 minutes.

14. The method of claim 10, wherein applying comprises applying electrical stimulation of between 0.25 and 5 mA to the vagus nerve for less than 2 minutes, followed by an off-time of at least 10 minutes.

15. The method of claim 10, further comprising continuously monitoring the patient for the biomarker.

16. The method of claim 10, further comprising diagnosing or identifying the patient suffering from a disorder involving demyelinated nerves.

17. A method of treating a demyelination disorder using an implantable system including a biosensor, a stimulator and a controller, the method comprising:

receiving data from the biosensor indicative of demyelination in a patient; and applying stimulation to a vagus nerve from the stimulator when the data from the biosensor is at a level that exceeds or falls below a predetermined threshold that indicates demyelination to decrease demyelination and/or to increase remyelination of the patient's nerves.

18. The method of claim 17, wherein applying comprises repeatedly applying a low duty-cycle electrical stimulation of between 0.25 and 5 mA to the patient's vagus nerve for less than 2 minutes, followed by an off-time of between 12 and 48 hours.

19. The method of claim 17, further comprising continuously monitoring the patient for demyelination.

20. The method of claim 17, further comprising monitoring the patient for a biomarker related to a disease selected from the group consisting of neurodegenerative diseases, neuroinflammatory diseases, and neuropathies.

21. An implantable system for treating a demyelination disorder, the implantable system comprising:

a biosensor configured to detect one or more biomarkers for demyelination;

a stimulator configured to apply stimulation to the vagus nerve; and a controller coupled to the biosensor and the stimulator and comprising control logic to control the activation of the stimulator, wherein the control logic is configured to apply a low duty-cycle electrical stimulation of less than 5 mA to the vagus nerve from the stimulator when the control logic determines that the biosensor detects the one or more biomarkers at a level that exceeds or falls below a predetermined threshold indicating demyelination.

22. The system of claim 21, wherein the biosensor is configured to detect a biomarker from the patient's blood and/or cerebrospinal fluid.

* * * * *